United States Patent
Asano et al.

(10) Patent No.: US 8,785,147 B2
(45) Date of Patent: Jul. 22, 2014

(54) L-THREONINE ANALYSIS METHOD AND L-THREONINE DEHYDROGENASE

(75) Inventors: Yasuhisa Asano, Imizu (JP); Techawaree Ueatrongchit, Imizu (JP)

(73) Assignees: Toyama Prefecture, Toyama (JP); Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/602,473

(22) Filed: Sep. 4, 2012

(65) Prior Publication Data

US 2013/0052679 A1 Feb. 28, 2013

Related U.S. Application Data

(63) Continuation of application No. PCT/JP2011/055134, filed on Mar. 4, 2011.

(30) Foreign Application Priority Data

Mar. 4, 2010 (JP) .................................. 2010-048193

(51) Int. Cl.
*C12Q 1/26* (2006.01)
(52) U.S. Cl.
USPC ............................................ 435/25; 435/189
(58) Field of Classification Search
None
See application file for complete search history.

(56) References Cited

FOREIGN PATENT DOCUMENTS

| JP | 2000-060572 | 2/2000 |
|---|---|---|
| JP | 2006-223166 | 8/2006 |

OTHER PUBLICATIONS

Database DDBJ/EMBL/GenBank [online], Accession No. AM260480, Region 927436..928392 <http://www.ncbi.nlm.nih.gov/nuccore/113528459?from=927436&to=928392&report=gbwithparts> Sep. 11, 2007 uploaded, [retrieved on Mar. 25, 2011] Pohlmann A. et al., Definition: Ralstonia eutropha H16 chromosome 2.
Database DDBJ/EMBL/GenBank [online], Accession No. NC_007348, Region 1502108..1503055 <http://www.ncbi.nlm.gov/nuccore/73537298?sat=OLD08&satkey=9258572> Apr. 25, 2009 uploaded, [retrieved on Mar. 25, 2011] Copeland A. et al., Definition: Ralstonia eutropha JMP134 chromosome 2, complete sequence.
Database DDBJ/EMBL/GenBank [online], Accession No. AAKL01000026, Region 10326..11282 <http://www.ncbi.nlm.nih.gov/nuccore/83725460?from=10326&to=11282&report=gbwithparts> Dec. 19, 2005 uploaded, [retrieved on Mar. 25, 2011] Gabriel D.W. et al., Definition: Ralstonia solanacearum UW551 Cont1001, whole genome shotgun sequence.
Nishida, T., et al., "A Specific Method for the Determination of Threonine in Rat Blood Plasma Using Aldehyde Dehydrogenase," J. Biochem. 1977;81:1085-1090.
Watanabe, K., et al., "Application of an Immobilized *Escherichia coli* Cell Tube in Analysis of L-Threonine," Agric. Biol. Chem. 1982;46(1):119-126.
International Preliminary Report on Patentability for PCT Patent App. No. PCT/JP2011/055134 (Oct. 11, 2012) with English translation thereof.
GenBank Accession No. AM260480, Ralstonia eutropha H16 chromosome 2, deposited Sep. 11, 2007; retrieved Mar. 25, 2011, pp. 1-2.
GenBank Accession No. NC_007348, Ralstonia eutropha JMP134 chromosome 2, complete sequence, deposited Apr. 25, 2009; retrieved Mar. 25, 2011, pp. 1-2.
Official Action from Chinese Patent App. No. 201180012376.9 (May 16, 2013) with English translation.
Official Action issued in Chinese Patent App. No. 201180012376.9 (Feb. 12, 2014) with English language translation thereof.

*Primary Examiner* — Nashaat Nashed
(74) *Attorney, Agent, or Firm* — Shelly Guest Cermak; Cermak Nakajima LLP

(57) ABSTRACT

A method for analyzing L-threonine contained in an specimen, which includes the steps of mixing a sample containing the specimen with an L-threonine dehydrogenase derived from *Cupriavidus necator* and a coenzyme NAD+ and analyzing the amount of NADH or 2-amino-3-oxobutyric acid after a predetermined period; an L-threonine dehydrogenase derived from *Cupriavidus necator*, which is a novel L-threonine dehydrogenase (TDH; EC 1.1.1.103) and can be utilized in the above-mentioned analysis method; a method for preparing a gene or the like to be used in the preparation of the enzyme, or a method for preparing the enzyme; an L-threonine analysis kit which includes (A) the L-threonine dehydrogenase and (B) a coenzyme NAD+; an enzyme preparation for use in the analysis of L-threonine, which includes the L-threonine dehydrogenase contained in a buffer solution; and an enzyme sensor utilizing the L-threonine dehydrogenase.

5 Claims, 7 Drawing Sheets

Fig. 9

```
         10        20        30        40        50        60
ATGGAAGGTGGCAAACGGAGATCCTGATTGTCGGTGCAACGGCAGATCGGTCGAR
 M  E  A  G  N  K  K  I  L  I  V  G  A  N  G  Q  I  G  S  E 70        80        90       100       110       120
CTGGCACTGGCGCTGGCCGAGCCTATGGCGCCACCAACGTGATCACTTCCGACGTGGTG
 L  A  L  A  L  A  E  R  Y  G  P  T  N  V  I  T  S  D  V  V 130       140       150       160       170       180
CCCACCGGCCGACATGTGCATCGACCTAGAGATGCTCAACGCCACCGACCGCGGCGAG
 P  T  G  R  H  V  H  L  T  R  E  M  L  N  A  T  D  R  G  E 190       200       210       220       230       240
CTGGCCACCGTGGTCGAGCGCCATGGCATCACCCAGGTCTACCTGCTGGCCGCCGCTG
 L  A  T  V  V  E  R  H  G  I  T  Q  V  Y  L  L  A  A  A  L 250       260       270       280       290       300
TCGGCCACCGGCGAAAAGGCCGCCCAGTGGGCCTGGAACCTCAATATGACCAGCCTGCTC
 S  A  T  G  E  K  A  P  Q  W  A  W  N  L  N  M  T  S  L  L 310       320       330       340       350       360
AATGTGCTGGAGCTGGCGCGGCAGACCGGGCTGGAGCGGGTGTTCTGGCCAAGCTCGATT
 N  V  L  E  L  A  R  Q  T  G  L  E  R  V  F  W  P  S  S  I 370       380       390       400       410       420
GCAGCCTTCGGCCCGACCACGTTCGCCGGACAGACGCCGCAGAAGACCGTGATGGAGCCT
 A  A  F  G  P  T  T  F  A  G  Q  T  P  Q  K  T  V  M  E  P 430       440       450       460       470       480
ACCACGGTCTACGGCATCTCCAGGCAGGCCGAGGGTTGGTGCCGCTGGTATCACGCC
 T  T  V  Y  G  I  S  R  Q  A  G  E  G  W  C  R  W  I  H  A 490       500       510       520       530       540
AACGGCGTGATGTGCGATCGTCGCTATCGGCCTGATCTCCCACAAGACCCA
 N  G  V  D  V  R  S  V  R  Y  P  G  L  I  S  H  K  T  P 550       560       570       580       590       600
CCCGGCGGCGGCACCACCGACTATGCGGTGGACATCTTCATCGCCGTGACCGGCGAG
 P  G  G  T  T  D  Y  A  V  G  I  F  H  A  A  V  T  G  E 610       620       630       640       650       660
CCCTGCACCTGCTTCCTGAAGGAGACCGAACCGCTCATGATGTATATGTCCGATGCG
 P  Y  T  C  F  L  K  E  D  E  A  L  P  M  Y  K  P  D  A 670       680       690       700       710       720
ATCCGCGCCACCATCGAACTGATGGAAGCCCCGGCCGACAAGCTGAGCGAGTGCGCAGC
 I  R  A  T  I  E  L  M  E  A  P  A  D  K  L  S  E  R  G 730       740       750       760       770       780
TACAACATCGCCGGCATGAGCTTCACGCCCGCCAGATCGCCGCGCCATCCGCGAGCAG
 Y  N  I  A  G  M  S  F  T  P  A  Q  I  A  A  A  I  R  E  Q 790       800       810       820       830       840
GTGCCGGCTTGCGATCCGTATGAACCGGACTATCGCCAGGCGATTGCGCAGGCTGG
 V  P  G  Q  I  R  Y  E  P  D  Y  R  Q  A  I  A  Q  G  W 850       860       870       880       890       900
CCGGATTCGATCGATGATTCGGTCGCGTGCGCGACTGGGGTGGAAGCCCAGTATGGA
 P  F  S  I  D  D  S  V  A  R  A  D  W  G  W  K  Q  Y  G 910       920       930       940       950
CTGAAGAGAGTCGCGGACATGCTTGCAACCTGAAGGCCACGCTGGCGTCA
 L  K  E  N  V  A  G  M  L  A  N  L  K  A  T  L  A  G  *
```

L-THREONINE ANALYSIS METHOD AND L-THREONINE DEHYDROGENASE

This application is a Continuation of, and claims priority under 35 U.S.C. §120 to, International Application No. PCT/JP2011/055134, filed Mar. 4, 2011, and claims priority therethrough under 35 U.S.C. §119 to Japanese Patent Application No. 2010-048193, filed Mar. 4, 2010, the entireties of which are incorporated by reference herein. Also, the Sequence Listing filed electronically herewith is hereby incorporated by reference. (File name: 2012-09-04_US-488_Seq_List; File size: 6 KB; Date recorded: Sep. 4, 2012).

BACKGROUND OF THE INVENTION

1. Field of the Invention

The present invention relates to a method for analyzing L-threonine, and also to L-threonine dehydrogenase that can be employed in this analysis method.

2. Brief Description of the Related Art

L-threonine, an essential amino acid, must be obtained from food. L-threonine is necessary to maintain the balance of nitrogen within the body and to promote healthy growth. It also performs functions in the cardiovascular system, liver, central nervous system, intestines, and immune system.

Vitamin B12 deficiency, type II citrullinemia, sepsis, and amino acid or nitrogen imbalances cause deficiencies in the threonine content of the blood. Further, when vegetarians eat grains with low quantities of threonine-containing materials, they sometimes develop threonine deficiencies. The quantification of L-threonine is required for the diagnosis of various illnesses and congenital metabolic disorders, providing long-term dietary supplements to patients, research relating to illnesses involving amino acid metabolic disorders, and the like.

Various methods of quantifying L-threonine have been reported. Protein hydrolysate, gelatin, and blood threonine can be quantified by the conversion of threonine to acetaldehyde by lead tetraacetate, absorption by concentrated sulfuric acid, the measurement of pigment generated by the condensation of p-hydroxybiphenyl and acetaldehyde, high performance liquid chromatography, mass spectrometry, amino acid analyzer, and the like. These methods present problems in that they are dangerous to operate, require numerous steps, utilize expensive equipment, and are not suited to mass screening involving the handling of large numbers of samples.

There is an enzymatic method that employs threonine deaminase (EC 4.2.1.16). This enzyme degrades L-threonine into α-ketobutyrate and ammonia. Thus, a method that converts the α-ketobutyrate that is produced into hydrazone derivatives has been reported (Watanabe K, Itoh N, Tanaka A, Fukui S. Application of an immobilized *Escherichia coli* cell tube in analysis of L-threonine. Agric. Biol. Chem. (1982) 46:119-126.).

There is an example in which threonine in rat plasma is oxidized by periodic acid, and the aldehyde produced is quantified by aldehyde dehydrogenase (EC 1.2.1.5). The remainder of the periodic acid is consumed by the addition of D-galactose (Nishida T, Kume S, Saito M, Suda M. A specific method for the determination of threonine in rat blood plasma using aldehyde dehydrogenase. J. Biochem. (1977) 81:1085-1090). Acetaldehyde produces NADH by the reduction of NAD+ through the action of aldehyde dehydrogenase, and is quantified by a method employing a fluorescent pigment.

However, in the method described in Watanabe et al. (Application of an immobilized *Escherichia coli* cell tube in analysis of L-threonine. Agric. Biol. Chem. (1982) 46:119-126), threonine deaminase has activity not just on L-threonine, but also on L-serine and D-serine. Thus, this method is unsuited to the quantification of samples containing L-serine and the like.

In the method described in Nishida et al. (A specific method for the determination of threonine in rat blood plasma using aldehyde dehydrogenase. J. Biochem. (1977) 81:1085-1090), the remaining periodic acid must be consumed by adding D-galactose. It is thus not a quantification method based on a single enzyme.

SUMMARY OF THE INVENTION

Accordingly, aspects of the present invention include providing a method for analyzing L-threonine that permits quantification based on a single enzyme; providing a novel L-threonine dehydrogenase (TDH; EC 1.1.1.103) that can be employed in this analysis method, a gene and the like that can be employed in the preparation of this enzyme, and a method for preparing the enzyme; and providing a kit and enzyme preparation which can be used in the above L-threonine analysis.

L-threonine quantification with TDH has not been previously reported. A novel TDH is described that can be used in methods of analyzing L-threonine. As a result, a novel TDH which is purified from, and hence native to, *Cupriavidus necator* was found, and using this TDH, a method which permits the enzymatic quantification of L-threonine was discovered.

It is an aspect of the present invention to provide a method for analyzing the L-threonine contained in a specimen, comprising:

A) mixing a sample comprising a specimen and L-threonine dehydrogenase, with the coenzyme NAD$^+$; and B) analyzing the quantity of a product after a time period, wherein the product is selected from the group consisting of NADH and 2-amino-3-oxybutyric acid;

wherein said L-threonine dehydrogenase has L-threonine dehydrogenase activity and is selected from the group consisting of:

(i) L-threonine dehydrogenase from *Cupriavidus necator*;

(ii) a protein comprising the amino acid sequence of SEQ ID NO: 1;

(iii) a protein comprising the amino acid sequence of SEQ ID NO: 1, but having from 1 to 30 amino acid deletions, substitutions, and/or additions; and (iv) a protein comprising an amino acid sequence having 90% or greater homology with the amino acid sequence of SEQ ID NO: 1.

It is a further aspect of the present invention to provide the method as described above, wherein the *Cupriavidus necator* is *Cupriavidus necator* NBRC 102504.

It is a further aspect of the present invention to provide the method as described above, wherein said determining comprises measuring absorbance ($A_{340}$) at 340 nm, generation of pigment, or conversion to fluorescence.

It is a further aspect of the present invention to provide the method as described above, wherein said determining comprises measuring the ammonia or hydrogen peroxide produced when monoamine oxidase is oxidized with the amino acetone produced from 2-amino-3-oxobutyric acid.

It is a further aspect of the present invention to provide L-threonine dehydrogenase from *Cupriavidus necator*.

It is a further aspect of the present invention to provide the L-threonine dehydrogenase as described above, wherein the *Cupriavidus necator* is *Cupriavidus necator* NBRC 102504.

It is a further aspect of the present invention to provide a protein having L-threonine dehydrogenase activity and comprising an amino acid sequence selected from the group consisting of:
  (i) the amino acid sequence of SEQ ID NO: 1 in the Sequence Listing;
  (ii) the amino acid sequence of SEQ ID NO: 1, but having from 1 to 30 amino acid deletions, substitutions, and/or additions; and
  (iii) an amino acid sequence having 90% or greater homology with the amino acid sequence of SEQ ID NO: 1.

It is a further aspect of the present invention to provide L-threonine dehydrogenase from *Cupriavidus necator* having the physical properties and characteristics set forth below:
  (i) molecular weight (SDS-PAGE and gel filtration chromatography): 79,400;
  (ii) subunit molecular weight (SDS-PAGE): 37,200;
  (iii) optimal pH: 10.0;
  (iv) optimal temperature: 75° C.;
  (v) substrate specificity: exhibits activity only to L-threonine;
  (vi) coenzyme: $NAD^+$ (no $NADP^+$ activity); and
  (vii) inhibitors: inhibited by iodoacetamide, PMS, and NEM.

It is a further aspect of the present invention to provide a gene encoding the protein as described above.

It is a further aspect of the present invention to provide a recombinant vector comprising the gene as described above.

It is a further aspect of the present invention to provide a transformant obtained by transforming a host cell with the gene described above.

It is a further aspect of the present invention to provide a transformant obtained by transforming a host cell with the recombinant vector as described above.

It is a further aspect of the present invention to provide a method for producing a protein having L-threonine dehydrogenase activity, comprising:
  (A) introducing the gene as described above into a vector;
  (B) transforming a host cell with the vector;
  (C) culturing the host cell so that a protein encoding by the gene is produced; and
  (D) collecting the protein.

It is a further aspect of the present invention to provide a kit for analyzing L-threonine, comprising:
  (A) L-threonine dehydrogenase having L-threonine dehydrogenase activity, wherein said L-threonine dehydrogenase is selected from the group consisting of:
    (i) L-threonine dehydrogenase from *Cupriavidus necator*;
    (ii) a protein comprising the amino acid sequence of SEQ ID NO: 1;
    (iii) a protein comprising the amino acid sequence of SEQ ID NO: 1, but having 1 to 30 amino acid deletions, substitutions, and/or additions; and
    (iv) a protein comprising an amino acid sequence having 90% or greater homology with the amino acid sequence of SEQ ID NO: 1; and
  (B) the coenzyme $NAD^+$.

It is a further aspect of the present invention to provide the kit as described above, wherein the *Cupriavidus necator* is *Cupriavidus necator* NBRC 102504.

It is a further aspect of the present invention to provide the kit as described above, further comprising an enzyme and/or a pigment for analyzing the quantity of NADH.

It is a further aspect of the present invention to provide a buffer preparation for analyzing L-threonine comprising a buffer and L-threonine dehydrogenase; wherein said L-threonine dehydrogenase has an activity of L-threonine dehydrogenase and is selected from the group consisting of:
  (i) L-threonine dehydrogenase from *Cupriavidus necator*;
  (ii) a protein comprising the amino acid sequence of SEQ ID NO: 1;
  (iii) a protein comprising the amino acid sequence of SEQ ID NO: 1, but with 1 to 30 amino acid deletions, substitutions, and/or additions; and
  (iv) a protein comprising an amino acid sequence having 90% or greater homology with the amino acid sequence of SEQ ID NO: 1.

It is a further aspect of the present invention to provide the buffer preparation as described above, wherein the *Cupriavidus necator* is *Cupriavidus necator* NBRC 102504.

It is a further aspect of the present invention to provide an enzyme sensor which is able to quantify L-threonine, comprising a detection-use electrode onto which L-threonine dehydrogenase is directly or indirectly immobilized; wherein said L-threonine dehydrogenase has L-threonine dehydrogenase activity and is selected from the group consisting of:
  (i) L-threonine dehydrogenase from *Cupriavidus necator*;
  (ii) a protein comprising the amino acid sequence of SEQ ID NO: 1;
  (iii) a protein comprising the amino acid sequence of SEQ ID NO: 1, but having 1 to 30 amino acid deletions, substitutions, and/or additions; and
  (iv) a protein comprising an amino acid sequence having 90% or greater homology with the amino acid sequence of SEQ ID NO: 1.

The present invention permits quantification of the concentration of L-threonine in a sample by dehydrogenating the L-threonine in a sample with TDH, reducing the coenzyme $NAD^+$ to quantitatively generate NADH, and directly or indirectly quantifying the NADH. The method of the present invention permits single-step analysis. Alternatively, it permits the quantification of the concentration of L-threonine by quantifying the 2-amino-3-oxobutyric acid generated from L-threonine by this enzymatic reaction.

BRIEF DESCRIPTION OF THE DRAWINGS

FIG. 9 shows the amino acid sequence (SEQ ID NO: 1) and gene sequence (SEQ ID NO 2) of the TDH of the present invention.

DESCRIPTION OF THE PREFERRED EMBODIMENTS

<L-Threonine Dehydrogenase>

Figure 1:
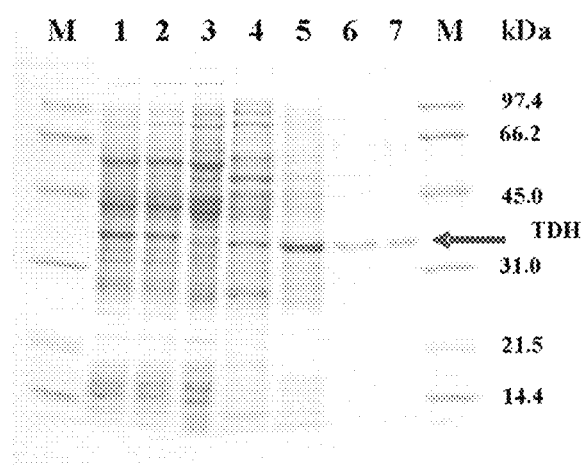
FIG. 1 shows the SDS-PAGE of *C. necator* NBRC 102504 derived TDH (SEQ ID NO: 1). Lanes: M: molecular weight standard s; 1: cell-free extract; 2: protamine sulfate; 3: 30 to 60% ammonium sulfate fraction; 4: Toyopearl DEAE; 5: Toyopearl butyl; 6: Gigapite; 7: Superdex-G200.

L-threonine dehydrogenase (TDH: EC 1.1.1.103) is an important key enzyme in the catabolism of L-threonine in microorganisms and animals [Reference Documents 1, 2]. TDH catalyzes the oxidation reaction of L-threonine to 2-amino-3-oxobutyric acid. 2-Amino-3-oxobutyric acid undergoes a nonenzymatic decarboxylation reaction and is decomposed into amino acetone and carbon dioxide. The amino acetone decomposes further into glycine and acetyl-CoA through the action of CoA-dependent 2-amino-3-oxobutyric acid CoA lyase (EC 2.3.1.29) [Reference Document 3].

[Chem. 1]

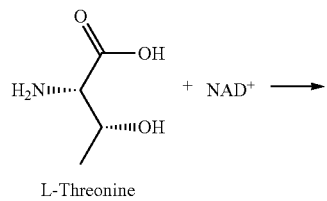

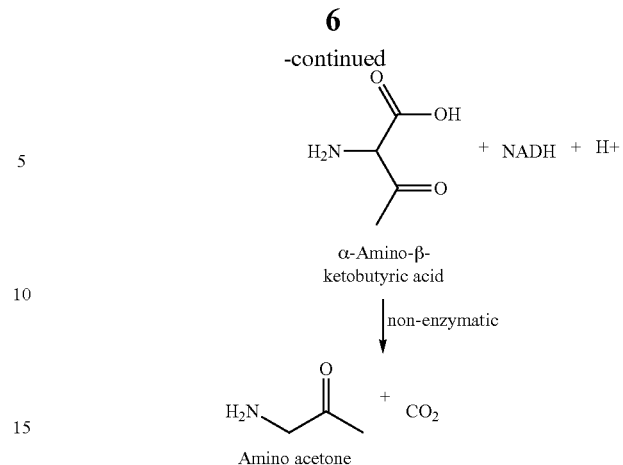

Scheme 1. Reaction catalyzed by L-threonine dehydrogenase

Microorganism-derived TDH has been discovered in the following microorganisms (Table 1). They are *Arthrobacter* sp., *E. coli* K12, *Cytophaga* sp. KUC-1, *Clostridium sticklandii*, *Pyrococcus furiosus*, *Pyrococcus horikoshii*, *Thermococcus kodakaraensis*, and *Streptomyces* sp. 139 [Reference Documents 4 to 10]. The TDH genes of the last four have been cloned and their genetic sequences are known and the enzymes have been expressed in *E. coli*.

The TDH of *E. coli*, *P. horikoshii*, and *T. kodakaraensis* requires $NAD^+$ and zinc as coenzymes. These belong to the super family of medium-chain alcohol dehydrogenases, which contain zinc [Reference Documents 8, 11, 12]. *Cytophaga*-derived TDH requires $NAD^+$ and its structure belongs to the superfamily of short-chain dehydrogenases/reductases, which are similar to UDP-glucose-4-epimerase. When *E. coli*-derived TDH is introduced into a heterogeneous host, the production of L-threonine is known to be effective.

The present inventors discovered a new $NAD^+$-dependent L-TDH (sometimes abbreviated to CnTDH hereinafter) from *Cupriavidus necator*. This enzyme has been purified to a uniform state and its various enzymatic and chemical properties have been determined. This enzyme employs $NAD^+$ as a coenzyme and catalyzes a dehydrogenation reaction specific to L-threonine. This enzyme does not require metal ions as cofactors. When the gene of this enzyme was cloned and its sequence was analyzed, it was found to exhibit only 57% homology with the TDH gene of *Cytophaga* sp. (now *Flavobacterium frigidimaris*) KUC-1. It has almost no homology with the genes reported for thermophilic bacteria and *E. coli*-derived TDH. This gene is expressed well in *E. coli*. When an His-tag was added to the N-terminus, this enzyme was expressed in large quantity and could be efficiently purified.

TABLE 1

Table 1. Various microorganism-derived L-threonine dehydrogenases and their uses

| Derivation | Purification and characterization | Gene cloning, expression, and characterization | Uses | L-threonine quantification |
|---|---|---|---|---|
| *Arthrobacter* sp. | 0 | X | X | X |
| *Escherichia coli* K-12 (other strains exist) | 0 | 0 | L-threonine production | X |
| *Cytophaga* sp. KUC-1 (now classified as *Flavobacterium frigidimaris*) | 0 | 0/X | X | X |
| *Clostridium sticklandii* | 0 | X | X | X |

TABLE 1-continued

Table 1. Various microorganism-derived L-threonine dehydrogenases and their uses

| Derivation | Purification and characterization | Gene cloning, expression, and characterization | Uses | L-threonine quantification |
|---|---|---|---|---|
| *Thermococcus kodakaraensis* | X | 0 | X | X |
| *Pyrococcus furiosus* | X | 0 | X | X |
| *Pyrococcus horikoshii* | X | 0 | X | X |
| *Streptomyces* sp. 139 | X | 0 | X | X |

In the table, "X" denotes "Not applicable" or "No actual results" and "0" denotes the existence of results, respectively.

The L-threonine dehydrogenase can be an L-threonine dehydrogenase derived from, or native to *Cupriavidus necator*. The *Cupriavidus necator* can be *Cupriavidus necator* NBRC 102504. *Cupriavidus necator* NBRC 102504 is a commercially available strain. *Cupriavidus necator* was once classified as *Alcaligenes eutrophus*, but has now been reclassified as *Cupriavidus necator*. *Cupriavidus necator* NBRC 102504 is a strain that was once commercially available as *Alcaligenes eutrophus* IAM 13533, but is now commercially available as *Cupriavidus necator* NBRC 102504. *Rastonia eutropha* and *Wautersia eutropha* are other strain names of *Cupriavidus necator*.

The L-threonine dehydrogenase can be a protein having any one of the amino acid sequences of (1) to (3) below and having L-threonine dehydrogenase activity:

(1) the amino acid sequence of SEQ ID NO: 1;
(2) the amino acid sequence of SEQ ID NO: 1, but including from 1 to 30 amino acid deletions, substitutions, and/or additions; and
(3) an amino acid sequence having 90% or greater homology with the amino acid sequence of SEQ ID NO: 1.

The amino acid sequence of SEQ ID NO: 1 is the amino acid sequence of a protein having L-threonine dehydrogenase activity obtained from *Cupriavidus necator* NBRC 102504. L-threonine dehydrogenase activity can be determined by the method described in the item "Screening and assaying for activity" in Example 1. The same applies below.

The protein having L-threonine dehydrogenase activity can have an amino acid sequence of SEQ ID NO: 1, but can have from 1 to 30 amino acid deletions, substitutions, and/or additions. There can be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions, amino acid deletions, and/or amino acid insertions, so long as the protein exhibits L-threonine dehydrogenase activity.

The protein having L-threonine dehydrogenase activity can have 90% or greater homology with the amino acid sequence of SEQ ID NO: 1. From the perspective of enhancing L-threonine dehydrogenase activity, the amino acid sequence can have a homology of 95% or greater, 96% or greater, 97% or greater, 98% or greater, or 99% or greater, with the amino acid sequence of SEQ ID NO: 1.

The L-threonine dehydrogenase can be derived from *Cupriavidus necator*, and can have the physical properties and characteristics set forth below:

molecular weight (SDS-PAGE and gel filtration chromatography): 79,400;
subunit molecular weight (SDS-PAGE): 37,200;
optimal pH: 10.0;
optimal temperature: 75° C.;
substrate specificity: exhibits active only to L-threonine;
coenzyme: $NAD^+$ (no $NADP^+$ activity); and
inhibitors: inhibited by iodoacetamide, PMS, and NEM.

A gene is described which can encode the protein having any one of the amino acid sequences of (1) to (3) above and having L-threonine dehydrogenase activity. A representative example of the gene is shown in SEQ ID NO: 2.

A sequence fully identical to the gene sequence of SEQ ID NO: 2 was recorded as the gene of NAD dependent epimerase_dehydratase by the decoding of the entire genomic sequence of *Rastonia eutropha* H16. The amino acid sequence of NAD dependent epimerase_dehydratase is 100% identical to the amino acid sequence of SEQ ID NO: 1. However, the name NAD dependent epimerase_dehydratase was given automatically without testing, and no biochemical testing was conducted. The error in the recognition of what the amino acid sequence and gene sequence of NAD dependent epimerase_dehydratase actually were only became apparent through the results of testing which is described in the instant specification.

The method of obtaining the L-threonine dehydrogenase is not specifically limited. The protein may be synthesized chemically, or may be prepared by genetic recombination techniques. When preparing a recombinant protein, a gene (DNA) coding for the particular protein is obtained as set forth further below. The DNA is introduced into a suitable expression system to produce the protein (L-threonine dehydrogenase).

L-threonine dehydrogenase can be prepared by a production method which includes the steps of inserting a gene coding for the L-threonine dehydrogenase protein into a vector, transforming a host cell with the vector, culturing the transformed host cell to accumulate the protein coding for the gene in a culture, and collecting the protein that has accumulated.

The method of obtaining the gene coding for the L-threonine dehydrogenase is not specifically limited. The gene coding for the L-threonine dehydrogenase can be prepared by any method known to a person having ordinary skill in the art, such as by chemical synthesis, bioengineering methods, or mutation induction based on the information on the amino acid sequence of SEQ ID NO: 1 and on the base sequence of SEQ ID NO: 2.

For example, for DNA having the base sequence of SEQ ID NO: 2, the method of contact with a drug serving as a mutagen, the method of UV irradiation, the method of bioengineering, and the like can be conducted. The site-specific mutation induction method, a bioengineering method, is a method permitting the introduction of specific mutation into a specific position and is thus useful. It can be carried out in accordance with the methods described in Molecular Cloning: A Laboratory Manual, $2^{nd}$ Ed., Cold Spring Harbor Laboratory, Cold Spring Harbor, N.Y., 1989 (abbreviated to "Molecular Cloning $2^{nd}$ Ed." hereinafter); Current Protocols in Molecular Biology, Supplements 1 to 38, John Wiley &

Sons (1987-1997) (abbreviated to "Current Protocols in Molecular Biology" hereinafter); and the like.

Suitable probes and primers can be prepared based on the information of the amino acid sequence of SEQ ID NO: 1 and the base sequence given in SEQ ID NO: 2. These probes and primers can then be used to screen a cDNA library of *Cupriavidus necator* NBRC 102504 to isolate the gene. The cDNA library can be prepared by the usual methods from *Cupriavidus necator* NBRC 102504.

The gene coding for the L-threonine dehydrogenase can be obtained by the PCR method. PCR is conducted using a pair of primers designed to amplify the base sequence of SEQ ID NO: 2 using a cDNA library of *Cupriavidus necator* NBRC 102504 as template. The PCR reaction conditions can be suitably established. For example, 30 cycles of a reaction cycle consisting of 30 seconds at 94° C. (denaturation), 30 second to 1 minute at 55° C. (annealing), and 2 minutes at 72° C. (elongation) can be conducted, after which a reaction can be conducted for 7 minutes at 72° C. Next, the amplified DNA fragment can be cloned into a suitable vector permitting amplification in a host such as *E. coli*.

The above operations of preparing probes and primers, constructing a cDNA library, screening the cDNA library, and cloning a target gene are known to persons having ordinary skill in the art. For example, they can be conducted according to the methods described in Molecular Cloning $2^{nd}$ Ed. and Current Protocols in Molecular Biology.

The gene can be inserted into a suitable vector for use. The type of vector is not specifically limited. For example, it can be an autonomously replicated vector (such as a plasmid), or one that is incorporated into the genome of a host cell during the course of introduction into the host cell, and replicated along with the chromosome into which it has been incorporated. Desirably, the vector can be an expression vector. In an expression vector, the gene can be functionally linked to the elements required for transcription (such as promoters). A promoter is a DNA sequence that exhibits transcription activity in a host cell and can be suitably selected based on the type of host cell.

Examples of promoters that can function in bacteria cells are the *Geobacillus stearothermophilus* maltogenic amylase gene, *Bacillus licheniformis* alpha-amylase gene, *Bacillus amyloliquefaciens* BAN amylase gene, and *Bacillus subtilis* alkaline protease gene, as well as *Bacillus pumilus* xylosidase gene promoters, phage lambda $P_R$ and $P_L$ promoters, and *E. coli* lac, trp, and tac promoters.

Examples of promoters that can function in mammalian cells are the SV40 promoter, MT-1 (metallothionein gene) promoter, and adenovirus 2 major late promoter. Examples of promoters that can function in insect cells are the polyhedrin promoter, P10 promoter, *Autographa californica* polyhedrosis basic protein promoter, Baculovirus immediate early gene 1 promoter, and the Baculovirus 39K delayed-early gene promoter. Examples of promoters that can function in yeast host cells are promoters derived from yeast glycolytic system cells, alcohol dehydrogenase gene promoters, TP11 promoter, and ADH2-4-c promoter. Examples of promoters that function in filamentous cells are ADH3 promoter and tpiA promoter.

As needed, the gene can be functionally joined to a suitable terminator. The recombinant vector containing the gene can also include elements such as polyadenylation signals (such as those derived from SV40 or the adenovirus 5E1b region) and transcription enhancer series (such as the SV40 enhancer). The recombinant vector containing the gene can further include a DNA sequence permitting replication of the vector in a host cell, one example of which is the SV40 replication origin (when the host cell is a mammalian cell).

The recombinant vector containing the gene can further include selection markers. Examples of selection markers are genes for which complements are lacking in the host cell, such as dihydrofolate reductase (DHFR) and the *Schizosaccaromyces pombe* TPI gene, and genes conferring resistance to drugs such as ampicillin, kanamycin, tetracycline, chloramphenicol, neomycin, and hygromycin. The methods used to splice the gene, promoter, and, as desired, terminator and/or secretion signal sequences and insert them into a suitable vector are known to persons having ordinary skill in the art.

The recombinant vector containing the gene can be introduced into a suitable host to prepare a transformant. The host cell into which the recombinant vector containing the gene is inserted can be any cell that is capable of expressing the gene. Examples include bacteria, yeast, fungus, and higher eukaryotic cells.

Examples of bacterial cells are gram-positive cells such as *Bacillus* and *Streptomyces*, and gram-negative cells such as *E. coli*. These cells can be transformed by the protoplast method or by a known method employing a competent cell. Examples for mammalian cells are HEK293 cells, HeLa cells, COS cells, BHK cells, CHL cells, and CHO cells. Methods of transforming mammalian cells and inducing the expression of DNA sequences that have been introduced into the cells are also known. For example, the electroporation method, calcium phosphate method, and lipofection methods can be employed.

Examples of yeast cells are cells belonging to *Saccharomyces* or *Schizosaccaromyces*, such as *Saccharomyces cerevisiae* and *Saccharomyces kluyveri*. Examples of methods of introducing the recombinant vector into the host cell are the electroporation method, spheroblast method, and lithium acetate method.

Examples of fungus cells are filamentous bacteria such as cells belonging to *Aspergillus, Neurspora, Fusarium*, and *Trichoderma*. When employing a filamentous bacterium as a host cell, transformation can be conducted by incorporating the DNA construct into the host chromosome to obtain a recombinant host cell. The DNA construct can be introduced into the host chromosome by known methods, such as by homologous recombination or heterogenous recombination.

When employing an insect cell as the host cell, a vector into which the recombinant gene has been introduced and a Baculovirus can be jointly introduced into the insect cell to obtain a recombinant virus in the supernatant of an insect cell culture. The recombinant virus can then be used to infect insect cells and expression of the protein can be induced (for example, Baculovirus Expression Vectors, A Laboratory Manual; and Current Protocols in Molecular Biology, Bio/Technology, 6, 47 (1988)).

For example, the *Autographa californica* nuclear polyhedrosis virus, a virus infecting insects of the family *Mamestra brassicae*, can be employed as the Baculovirus.

Sf9 and Sf21, which are ovarian cells of *Spodoptera frugiperda* (Baculovirus Expression Vectors, A Laboratory Manual, W.H. Freeman and Company, New York (1992); HiFive (made by (nitrogen)), which are Trichoplusiani ovarian cells, and the like can be employed as insect cells.

The calcium phosphate method and lipofection method are examples of methods of jointly introducing a recombinant gene introduction vector and Baculovirus into an insect cell to prepare a recombinant virus.

The above transformant can be cultured in a suitable culture medium under conditions permitting the expression of the gene that has been introduced. The usual protein isolation and purification methods can be employed to isolate and purify the protein from the transformant culture. For example, when the protein has been expressed in a dissolved state within the cell, culturing is terminated, the cells are recovered by centrifugal separation and suspended in an aqueous buffer, the cells are disrupted with an ultrasonic disrupter or the like, and a cell-free extract is obtained. The cell-free extract is centrifugally separated to obtain a supernatant, from which the L-threonine dehydrogenase can be obtained as a purified product by the usual protein isolation and purification methods, employed singly or in combination. These methods include solvent extraction, salting out with ammonium sulfate, desalting, precipitation from an organic solvent, anion exchange chromatography employing a resin such as diethylaminoethyl (DEAE) Sepharose, cation exchange chromatography employing a resin such as S-Sepharose FF (made by Pharmacia), hydrophobic chromatography employing a resin such as Butyl-Sepharose or Phenyl-Sepharose, gel filtration employing a molecular sieve, affinity chromatography, chromatofocusing, and electrophoresis methods such as isoelectric electrophoresis.

<The Method for Analyzing L-Threonine>

The method for analyzing L-threonine can include the steps of mixing a sample containing a specimen, the L-threonine dehydrogenase, and coenzyme $NAD^+$, and analyzing the quantity of NADH after a prescribed period.

The L-threonine dehydrogenase can be L-threonine dehydrogenase derived from *Cupriavidus necator* NBRC 102504 (SEQ ID NO: 1).

The specimen is not specifically limited. For example, it can be human blood or a food or drink product.

The sample containing a specimen can be a mixture of the specimen with, for example, a buffer exhibiting an optimal pH for L-threonine dehydrogenase. The optimal pH for L-threonine hydrogenase is 10.0. In the course of analysis, a prescribed quantity of L-threonine dehydrogenase is added to the sample containing the specimen. The quantity of L-threonine dehydrogenase that is added is suitably determined taking into account the degree of purification and titer of the L-threonine dehydrogenase. For example, it can range from 0.001 to 1 U/200 µL.

In addition to L-threonine dehydrogenase, coenzyme $NAD^+$ is added to the sample containing the specimen. The coenzyme $NAD^+$ can be a salt of NAD, such as an alkali metal salt of sodium or potassium. The quantity of coenzyme $NAD^+$ that is admixed can be suitably determined taking into account the L-threonine concentration, titer of the L-threonine dehydrogenase, and the like in the sample. For example, it can range from 0.001 to 3 mM. $NAD^+$ is nicotinamide adenine dinucleotide, and is sometimes denoted as $\beta$-$NAD^+$—the two are synonymous. $NADP^+$ is also sometimes denoted as $\beta$-$NADP^+$—the two are also synonymous.

Once the L-threonine dehydrogenase and coenzyme $NAD^+$ have been mixed, the quantity of NADH is analyzed after a prescribed time. The prescribed time can be suitably determined taking into account the reaction temperature, concentration of L-threonine contained in the specimen, analysis precision, and the like. Normally, it ranges from 5 seconds to 60 minutes, or from 1 to 60 minutes.

After the prescribed period has elapsed, the quantity of NADH that has been produced by the L-threonine dehydrogenase is analyzed. The quantity of NADH can be directly analyzed by measuring the absorbance ($A_{340}$) at 340 mm, for example, or using an NADH pigment generating method, NADH fluorescence generating method, or the like. An example of an NADH pigment generating method is the method employing electron carriers in an $NADH^-$ tetrazolium system. PMS (phenazine methosulfate, +0.08 V) or Meldola's blue can be employed as the electron carrier. Examples of methods of generating pigments from NADH are methods employing diaphorase. In methods employing diaphorase, the diaphorase catalyzes the oxidation of NADH and the reduction of pigment, generating color. The pigment employed can be INT (2-(4-iodophenyl)-3-(4-nitrophenyl)-5-phenyltetrazolium chloride), NBT (nitroblue tetrazolium), or the like. A fluorescent pigment such as resazurin (7-hydroxy-3H-phenoxazin-3-one 10-oxide) can be employed in methods employing diaphorase.

The method for analyzing L-threonine can employ microplates and so-called microplate assays. A 96-well microplate can be employed, for example. The number of wells is not specifically limited. When employing a 96-well microplate, the total reaction volume is 200 µL, for example, and 100 mM of glycine KCl—KOH buffer (pH 10.0), 2.5 mM $NAD^+$, and deproteinized sample are added. The reaction is started by adding the L-threonine dehydrogenase. For example, the temperature can be maintained at 30° C. for 10 to 30 minutes, and the end point absorbance at 340 nm can be measured with a UV microplate spectrophotometer. The change ($\Delta A$) in absorbance is obtained by subtracting a control value from the final absorbance. The deproteinized sample is prepared by, for example, ultrafiltration with a Centricon YM-10.

The method for analyzing L-threonine can also be implemented by analyzing the quantity of 2-amino-3-oxobutyric acid produced from L-threonine by the L-threonine dehydrogenase. As shown in Scheme 1 above, the 2-amino-3-oxobutyric acid ($\alpha$-amino-$\beta$-ketobutyric acid) that is generated from L-threonine is nonenzymatically decarboxylated to generate amino acetone. The amino acetone becomes methylglyoxal through oxidation by monoamine oxidase. In that process, ammonia and hydrogen peroxide are produced. The ammonia and hydrogen peroxide that are produced can be quantified by known quantifying methods to quantify the L-threonine.

In addition to analyzing the quantity of NADH or 2-amino-3-oxobutyric acid, as shown in Scheme 1 above, it is also possible to implement the method for analyzing L-threonine by analyzing the quantity of $H^+$ generated with the 2-amino-3-oxobutyric acid and NADH by L-threonine dehydrogenase. The $H^+$ can be quantified by known quantifying methods.

<Kit for Analyzing L-Threonine>

A kit for analyzing L-threonine that contains (A) and (B) below is also described:

(A) L-threonine dehydrogenase derived from *Cupriavidus necator* and having L-threonine hydrogenase activity, wherein said L-threonine dehydrogenase has an amino acid sequence such as:
  (1) the amino acid sequence of SEQ ID NO: 1,
  (2) the amino acid sequence of SEQ ID NO: 1, but having 1 to 30 amino acid deletions, substitutions, and/or additions, or
  (3) an amino acid sequence having 90% or greater homology with the amino acid sequence of SEQ ID NO: 1,
  and
(B) the coenzyme $NAD^+$.

The *Cupriavidus necator* can be *Cupriavidus necator* NBRC 102504. The protein having the amino acid sequence of any one of (1) to (3) above and having L-threonine hydrogenase activity is identical to that described above.

The coenzyme $NAD^+$ of (B) can be $NAD^+$, for example. The kit can further include a pigment and/or enzyme for use in analyzing the quantity of NADH. The pigment for use in analyzing the quantity of NADH can be a pigment that develops color when reduced by an electron carrier or the above-described diaphorase. The kit may also contain a buffer suited to the enzyme. The buffer can contain the enzyme.

The kit may also be accompanied by a microplate, an ultrafiltration device employed to deproteinize the sample being analyzed, and a manual for the kit.

The present invention can further include an enzyme preparation for analyzing L-threonine, wherein L-threonine dehydrogenase derived from *Cupriavidus necator* or an enzyme having the amino acid sequence of any one of (1) to (3) below and having L-threonine dehydrogenase activity is incorporated in a buffer:

(1) the amino acid sequence of SEQ ID NO: 1

(2) the amino acid sequence of SEQ ID NO: 1, but having 1 to 30 amino acid deletions, substitutions, and/or additions, or (3) an amino acid sequence having 90% or greater homology with the amino acid sequence of SEQ ID NO: 1.

The L-threonine dehydrogenase derived from *Cupriavidus necator* is identical to that set forth above. The enzyme having the amino acid sequence of any one of (1) to (3) above and having L-threonine dehydrogenase activity is identical to that set forth above. The buffer into which the L-threonine dehydrogenase is incorporated can have a composition and pH that are suited to the L-threonine dehydrogenase.

<Enzyme Sensor>

The enzyme sensor of the present invention is employed to quantify L-threonine and is characterized in that L-threonine dehydrogenase derived from *Cupriavidus necator* or a protein having the amino acid sequence of any one of (1) to (3) below and having L-threonine dehydrogenase activity is directly or indirectly immobilized or disposed on a detection-use electrode:

(1) the amino acid sequence of SEQ ID NO: 1, (2) the amino acid sequence of SEQ ID NO: 1, but having 1 to 30 amino acid deletions, substitutions, and/or additions, or (3) an amino acid sequence having 90% or greater homology with the amino acid sequence of SEQ ID NO: 1.

The protein having the amino acid sequence of any one of (1) to (3) below and having L-threonine dehydrogenase activity is identical to that set forth above.

L-threonine dehydrogenase can be directly or indirectly immobilized or disposed on a detection-use electrode in the enzyme sensor, which can be used to quantify L-threonine. The enzyme sensor can be capable of directly detecting the quantity of product produced from L-threonine by L-threonine dehydrogenase. Additionally, in the enzyme sensor, in addition to the above enzyme, an electrochemical mediator that readily accepts and donates electrons between the enzyme and an electrode can be directly or indirectly immobilized or disposed on a detection-use electrode. The rest of the configuration can be identical to that employed in known enzyme sensors or employ suitable modifications. In the enzyme sensor, at least the detection-use electrode portion is immersed in a test solution containing a specimen, and the detection-use electrode detects the product produced from L-threonine by L-threonine dehydrogenase in the test solution. More specifically, an electrode that is capable of detecting NADH, which is one product produced from L-threonine, can be employed in combination with L-threonine dehydrogenase. As an electrode capable of detecting NADH, diaphorase or NADH oxidase can be combined with the above-described electrochemical mediator (electron carrier). The L-threonine dehydrogenase, diaphorase, and NADH oxidase can be used in free form, or can be directly or indirectly immobilized on the electrode by a known method. Examples of additional electrodes that are capable of detecting NADH are described in Japanese Unexamined Patent Publication (KOKAI) Heisei Nos. 7-280769 and 7-310194. These examples are not intended as limitations.

In addition to analyzing the quantity of NADH in this manner, the enzyme sensor can be configured to detect the quantity of 2-amino-3-oxobutyric acid that is produced from L-threonine by L-threonine dehydrogenase. As indicated in Scheme 1 above, the amino acetone that is nonenzymatically generated by decarboxylation from the 2-amino-3-oxobutyric acid ($\alpha$-amino-$\beta$-ketobutyric acid) that is produced from L-threonine is oxidized by monoamine oxidase to produce hydrogen peroxide, and the enzyme sensor can be used with a detection-use electrode in the form of a hydrogen peroxide electrode that is capable of quantifying this hydrogen peroxide. The enzyme sensor can be configured with a combination of L-threonine dehydrogenase and monoamine oxidase on the hydrogen peroxide electrode.

EXAMPLES

The present invention is further described below through the following non-limiting examples.

Example 1

Screening for Bacteria that Utilize L-Threonine

Bacteria that utilize L-threonine were obtained by screening the bacteria on deposit at Toyama Prefectural University. These bacteria were precultured aerobically for 3 days at 30° C. and 300 rpm in a medium of the following composition with L-threonine as the sole carbon and nitrogen source. The medium contained the following, per liter: 10 g of L-threonine, 2 g of $K_2HPO_4$, 1 g of NaCl, 0.1 g of $MgSO_4.7H_2O$, 4 µm of thiamine-HCl, 2 µm of riboflavin, 4 µg of calcium pantothenate, 4 µg of pyridoxine-HCl, 20 pg of biotin, 2 µm of p-aminobenzoic acid, 4 µg of nicotinic acid, 0.1 µg of folic acid, 20 µg of inositol, 500 µg of Titriplex IV, 200 µg of $FeSO_4.7H_2O$, 10 µg of $ZnSO_4.7H_2O$, 3 µg of $MnCl_2.4H_2O$, 30 µg of $H_3BO_4$, 20 µg of $CoCl_2.6H_2O$, 1 µg of $CuCl_2.2H_2O$, 2 µg of $NiCl_2.6H_2O$, and 3 µg of $Na_2MoO_4$.

The colonies that were separated were cultured under the same conditions using the above medium. The bacterial cells were centrifugally separated for 10 minutes at 28,400×g, washed twice with a 0.85% NaCl aqueous solution, and suspended in a 1 mL of a 100 mM potassium phosphate buffer (pH 7.4). The cells were disrupted with a Bead Shocker (2,700 rpm, on time 60 seconds, off time 60 seconds, 3 cycles, YGB01 glass beads 0.1 mm, 4° C.), and then centrifuged for 10 minutes at 4° C. and 28,400×g. A crude enzyme extract was thus prepared and its enzymatic activity was assayed.

Screening and Assaying for Activity

A standard dehydrogenated enzyme activity assay was conducted at 30° C. with a 96-well culture plate made by Greiner. The reaction mixture contained 20 µL of crude enzyme extract, $NAD^+$ (final concentration 2.5 mM), L-threonine (final concentration 10 mM), and glycine-KCl—KOH buffer (pH 10.4, final concentration 100 mM) to make a total volume of 200 µL. The NADH produced by reduction of $NAD^+$ was measured at 340 nm with a microplate reader. A value of 6.22 $mM^{-1}$ $cm^{-1}$ was employed as the molecular extinction coefficient of NADH. The enzymatic activity of 1 unit (U) under the above standard conditions was defined as the amount of enzyme that produced 1 µmol of NADH in 1 minute.

Quantifying the Protein Concentration

The protein concentration was determined using a BioRad protein assay kit or by absorbance at 281 nm with bovine serum albumin as the standard.

Results

TDH activity was detected in six of the 416 strains of bacteria deposited at Toyama Prefectural University (TPU) (Table 2). Strong TDH activity (1.97 and 1.01 U/mg, respectively) was detected in *Cupriavidus necator* (NBRC 102504 and IAM 13549). TDH activity was also detected at levels of 0.12, 0.08, 0.08, and 0.13 U/mg in the cell-free extracts of *Cedecea neteri* (JCM5909), *Arthrobacter bergeri* (NBRC 12127), *Enterobacter aerogenes* (NBRC 13534), and *Terrabacter tumescens* (NBRC 12960), respectively. Specificity to L-threonine was tested with standard microplate assays for L amino acids (L-alanine, L-arginine, L-asparagine, L-aspartic acid, L-cysteine, L-glutamic acid, L-glutamine, glycine, L-histidine, L-isoleucine, L-leucine, L-lysine, L-methionine, L-ornithine, L-phenylalanine, L-proline, L-serine, taurine, L-tryptophan, L-tyrosine, L-threonine, and L-valine). Under specificity to L-threonine, the term "present" indicates that there was L-threonine activity.

TABLE 2

Table 2. L-threonine dehydrogenase activity in cell-free extract of bacteria on deposit at TPU and bacteria separated from soil

| Bacterial strain | TPU No.* | Culture stock No. | Specific activity (U/mg) | Specificity to L-threonine |
|---|---|---|---|---|
| Cupriavidus necator | TPU 5305 | NBRC 102504 | 1.97 | present |
| Cupriavidus necator | TPU 5308 | IAM 13549 | 1.01 | present |
| Cedecea neteri | TPU 5752 | JCM 5909 | 0.12 | present |
| Arthrobacter bergerei | TPU 5709 | NBRC 12127 | 0.08 | present |
| Enterobacter aerogenes | TPU 6151 | NBRC 13534 | 0.08 | present |
| Terrabacter tumescens | TPU 6900 | NBRC 12960 | 0.13 | present |

*TPU No.: Bacterial deposit number at Toyama Prefectural University

The crude extract of *Cupriavidus necator* (NBRC 102504) exhibited the greatest specific activity, so the following detailed testing was conducted. These strains all exhibited high substrate specificity for L-threonine.

Growth conditions derived from *Cupriavidus necator* (NBRC 102504) and the purification of L-threonine dehydrogenase The preculturing of *C. necator* (NBRC 102504) was conducted overnight with shaking at 37° C. in 5 mL of TGY-T medium (0.5% of polypeptone, 0.5% of yeast extract, 0.1% of glucose, 0.1% of $K_2HPO_4$, 0.5 to 1% of L-threonine, pH 7.0). Medium (5 mL) from the preculture was cultured for 12 hours at 37° C. in 500 mL of the same medium. The bacterial cells were harvested and resuspended in 100 mM potassium phosphate buffer (pH 7.0).

Purification of TDH

The bacterial cells were disrupted in an ultrasonic processor for 20 minutes at 4° C. and centrifuged for 15 minutes at 28,000×g to remove the cell debris. The cell-free extract was fractionated, yielding enzyme activity in the 30 to 60% ammonium sulfate saturated portion. This fraction was dialyzed against potassium phosphate buffer (10 mM, pH 7.0). The enzyme solution was purified into a single by conventional methods such as a Toyopearl-DEAE 650M column of ion-exchange resin, hydrophobic chromatography in the form of Toyopearl-Butyl column chromatography, and Superdex-200 column chromatography.

Activity Assay

L-threonine oxidation activity was determined by measuring coenzyme $NAD^+$ reduction at 30° C. and 340 nm. The reaction composition consisted of a total volume of 1 mL and contained L-threonine (final concentration 10 mM), $NAD^+$ (final concentration 2.5 mM), and glycine-KCl—KOH buffer (100 mM, pH 10.0). The measurement of activity began with the addition of the enzyme. One unit (U) of enzymatic activity was defined as the amount of enzyme producing 1 μmol of NADH per minute under standard conditions.

Results

The purification steps of TDH derived from *C. necator* have been organized into Table 3. The enzyme was purified to homogeneity, with 6.4% yield and 75.4 purification fold. The purified TDH catalyzed the L-threonine dehydrogenase reaction with $NAD^+$ as coenzyme under standard conditions (specific activity: 42.2 U/mg).

TABLE 3

Table 3. Purification steps of TDH derived from *Cupriavidus necator* NBRC 102504

| Step | Total volume (mL) | Total activity (U) | Total protein (mg) | Specific activity (U/mg) | Yield (%) | Purification (fold) |
|---|---|---|---|---|---|---|
| Cell-free extract | 380 | 1,585 | 2,819.0 | 0.56 | 100.0 | 1.0 |
| Nuclease removed (protamine treatment) | 375 | 1,627 | 2,737.0 | 0.59 | 102.0 | 1.1 |
| 30-60% $(NH_4)_2SO_4$ | 53 | 1,201 | 1,767.0 | 0.68 | 75.8 | 1.2 |
| Toyopearl-DEAE | 130 | 660 | 330.0 | 2.00 | 41.6 | 3.6 |
| Toyopearl-Butyl | 46 | 395 | 42.3 | 9.34 | 24.9 | 16.7 |
| Gigapite | 149 | 402 | 12.4 | 32.50 | 25.4 | 58.1 |
| Superdex-G200 | 89 | 102 | 2.4 | 42.20 | 6.4 | 75.4 |

Measurement of Molecular Weight of TDH and Subunits

Various standard proteins were employed to determine the molecular weight of TDH according to the conventional methods using SDS-PAGE and gel filtration chromatography.

Results

Figure 2:
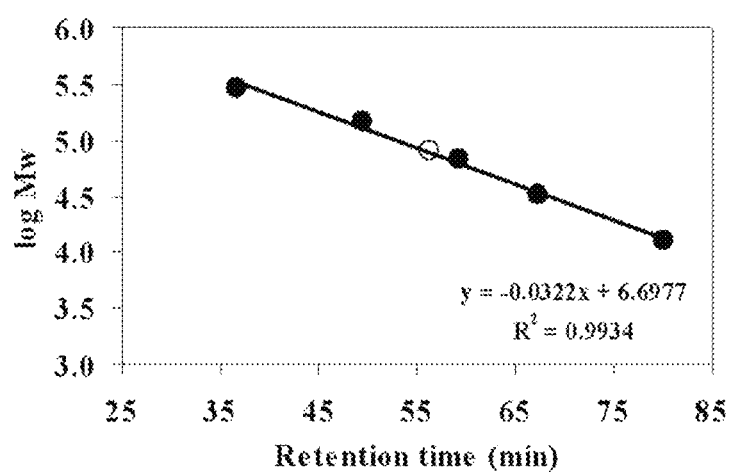
FIG. 2 shows molecular weight determination results for TDH. Standard protein (●), TDH(○).

The enzyme that had been purified through the final purification step exhibited a single band in SDS-PAGE. Its molecular weight was calculated to be 37,200 (FIG. 1). The native molecular weight was determined to be 79,400 by HPLC (FIG. 2). Thus, the dimer state was thought to be an active form of the native enzyme. As indicated in Table 4, the enzyme exhibited the native and subunit molecular weights of TDH derived from *Clostridium sticklandii* and chicken liver, but had a molecular weight that was different from the enzymes derived from others.

TABLE 4

Table 4. A comparison of the molecular weight and subunit weight of L-threonine dehydrogenase derived from Cupriavidus necator NBRC 102504

| TDH | Native Mw | Subunit Mw | Structure | Reference document |
|---|---|---|---|---|
| CnTDH | 79,400 | 37,200 | Homodimer | Present invention |
| CsTDH | 67,000 | 33,000 | Homodimer | [6] |
| Gd TDH | 62-74,000 | 36,000 | Homodimer | [2] |
| PfTDH | 155,000 | 37,823 | Homotetramer | [7] |

TABLE 4-continued

Table 4. A comparison of the molecular weight and subunit weight of L-threonine dehydrogenase derived from Cupriavidus necator NBRC 102504

| TDH | Native Mw | Subunit Mw | Structure | Reference document |
|---|---|---|---|---|
| EcTDH | 140,000 | 35,000 | Homotetramer | [11] |
| CyTDH | 139,000 | 35,000 | Homotetramer | [5] |

Abbreviations:
ND: not determined;
CsTDH: TDH from *Clostridium sticklandii*;
GdTDH: TDH from chicken liver (*Gallus domesticus*);
PfTDH: TDH from *Pyrococcus furiosus*;
EcTDH: TDH from *Escherichia coli* K-12;
CyTDH: TDH from *Cytophage* sp. KUC-1.

The effects of pH and temperature on enzymatic activity and stability

Enzymatic reactions were conducted in buffers of various pH levels.

Results

Figure 3:
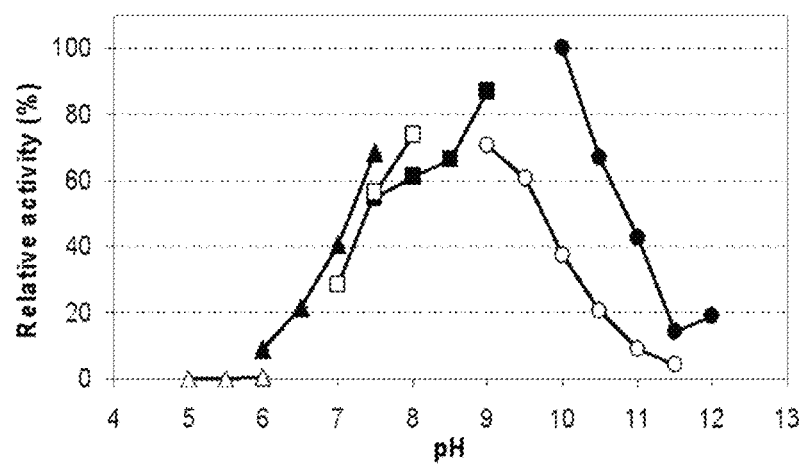
FIG. 3 shows TDH activity at various pH levels: (Δ) sodium acetate buffer (pH 5.0 to 6.0); (▲) potassium phosphate buffer (pH 6.0 to 7.5); (□) HEPES buffer (pH 7.0 to 8.0); (■) Tris-HCl buffer (pH 7.5 to 9.0; (○) $Na_2CO_3$—$NaHCO_3$ buffer (pH 9.0 to 11.5); (●) glycine-KCl—KOH buffer (pH 10.0 to 12.0).

The effect of pH on enzymatic activity was examined in various buffers. The optimal pH was determined as 10.0 in 100 mM glycine-KOH buffer (FIG. 3).

Figure 4:
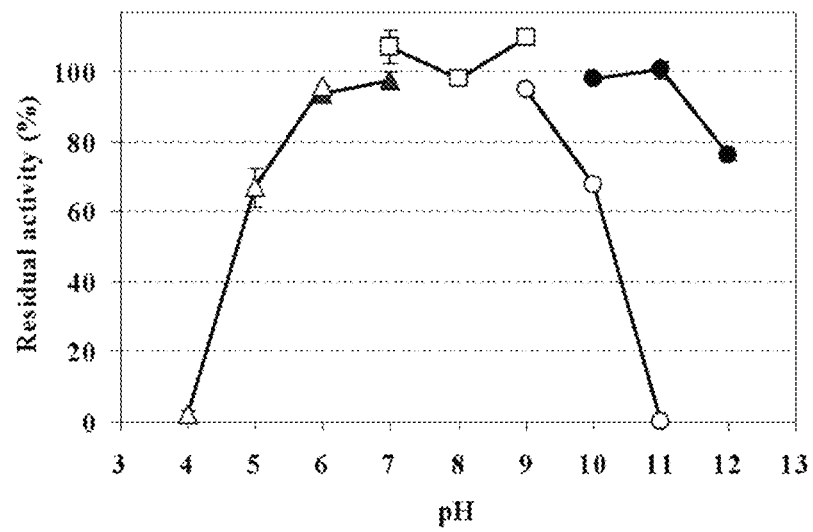
FIG. 4 shows the pH stability of TDH in various buffers. (Δ) sodium acetate buffer (pH 4.0 to 6.0); (a) potassium phosphate buffer (pH 6.0 to 7.5); (□)Tris-HCl buffer (pH 7.0 to 9.0; (○) $Na_2CO_3$—$NaHCO_3$ buffer (pH 9.0 to 11.0); (●) glycine-KCl—KOH buffer (pH 10.0 to 12.0).

The stability of TDH was examined using buffers of various pH levels. The TDH was maintained at constant temperature for 60 minutes at various pH levels and the residual activity of the enzyme was measured under standard conditions. The enzyme was extremely stable at pH 6 to 11 (FIG. 4). The enzyme was somewhat unstable in sodium acetate buffer (pH 4 to 5) and $Na_2CO_3$—$NaHCO_3$ buffer (pH 10 to 11).

Figure 5:
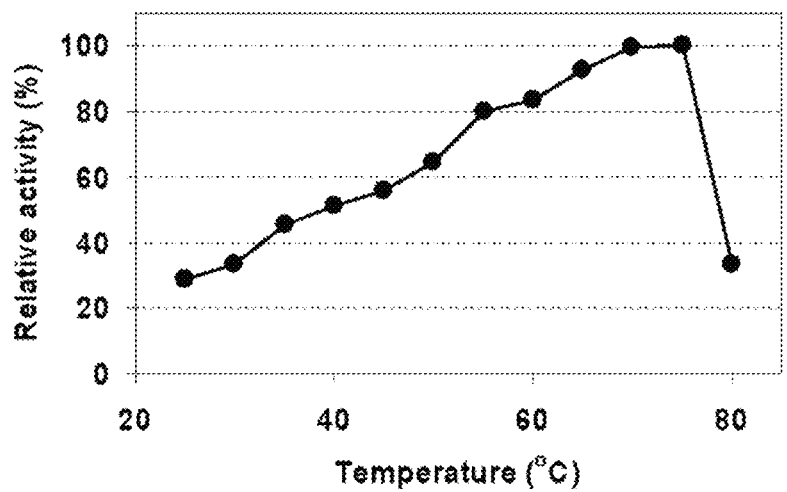
FIG. 5 shows the effect of temperature on TDH activity.

The TDH activity increased as the temperature was raised from 25 to 75° C. The optimal temperature for the TDH was 75° C. TDH activity was lost at 80° C. (FIG. 5).

Figure 6:
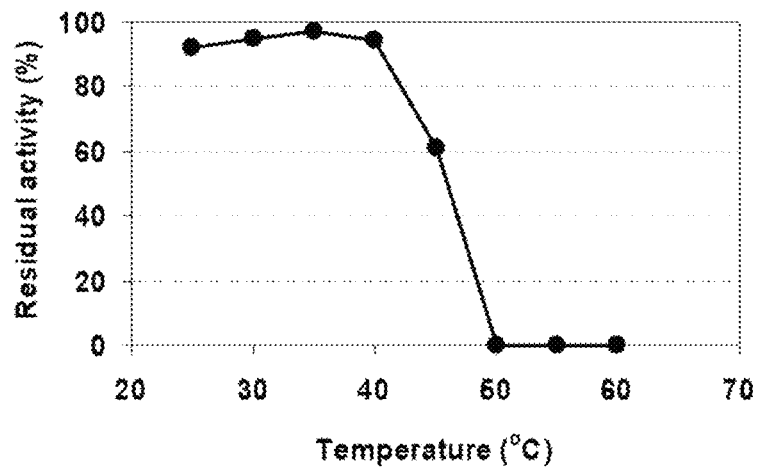
FIG. 6 shows the effect of temperature on enzyme stability.

The TDH was maintained at constant temperature for 60 minutes at various temperatures, after which the residual activity was determined. The enzyme was stable at 40° C. (FIG. 6). When kept at 45° C. for 60 minutes, 60% of the enzymatic activity remained. When maintained for 60 minutes at 50° C., enzymatic activity was completely lost.

Substrate Specificity

TDH was examined using substrates in the form of various L-amino acids, amino alcohols, and alcohols. The substrate concentration was 10 mM and activity was measured under standard assay conditions.

Results

Table 5 gives the substrate specificity of TDHs. The present enzyme exhibited the activity for only L-threonine and no activity was observed for D-threonine. The present enzyme did not also employ other L-amino acids, glycerol, amino alcohols, alcohols, or the like as substrates. No activity of the enzyme was observed with $NADP^+$ as coenzyme, although the enzyme showed the activity with $NAD^+$ as coenzyme.

TABLE 5

Table 5. A comparison of the substrate specificity of TDH derived from Cupriavidus necator NBRC 102504 (SEQ ID NO: 1) and TDH derived from other strains

| | Relative activity (%) | | | | |
|---|---|---|---|---|---|
| Substrate | CnTDH | CyTDH | CsTDH | EcTDH | StTDH |
| Amino acids | | | | | |
| L-threonine | 100 | 100 | 100 | 100.0 | 100 |
| DL-threonine | 64 | ND. | ND. | ND. | ND. |
| D-threonine | 0 | 0 | 0 | 63.7 | ND. |
| L-serine | 0 | 0 | 0 | 4.0 | ND. |
| L-serine (100 mM) | 0 | ND. | ND. | ND. | ND. |
| D-serine | 0 | ND. | ND. | ND. | ND. |
| DL-allothreonine | 0 | ND. | 0 | 95.0 | ND. |
| D-allothreonine | 0 | 0 | 0 | ND. | ND. |
| L-alanine | 0 | 0 | 0 | ND. | ND. |
| L-arginine | 0 | 0 | 0 | ND. | ND. |
| L-asparagine | 0 | 0 | 0 | ND. | ND. |
| L-aspartic acid | 0 | 0 | 0 | ND. | ND. |
| L-glutamic acid | 0 | 0 | 0 | ND. | ND. |
| L-glutamine | 0 | 0 | 0 | ND. | ND. |
| Glycine | 0 | 0 | 0 | ND. | ND. |
| L-histidine | 0 | 0 | 0 | ND. | ND. |
| L-isoleucine | 0 | 0 | 0 | ND. | ND. |
| L-lysine | 0 | 0 | 0 | ND. | ND. |
| L-methionine | 0 | 0 | 0 | ND. | ND. |
| L-ornithine | 0 | ND. | ND. | ND. | ND. |

Abbreviations:
ND.: not determined;
CyTDH: TDH from *Cytophaga* sp. KUC-1;
CsTDH: TDH from *Clostridium sticklandii*;
EcTDH: TDH from *Escherichia coli* K-12;
StTDH: TDH from *Streptomyces* sp. 139;

| | Relative activity (%) | | | |
|---|---|---|---|---|
| Substrate | PfTDH | AgTDH | TkTDH | GdTDH |
| Amino acids | | | | |
| L-threonine | 100 | 100 | 100 | 100 |
| DL-threonine | ND. | ND. | ND. | ND. |
| D-threonine | 5 | ND. | ND. | 0 |
| L-serine | 15 | ND. | 13 | 0 |
| L-serine (100 mM) | ND. | ND. | ND. | ND. |
| D-serine | ND. | ND. | ND. | ND. |
| DL-allothreonine | ND. | ND. | ND. | 0 |
| D-allothreonine | ND. | ND. | ND. | ND. |
| L-alanine | 0 | ND. | ND. | ND. |
| L-arginine | 0 | ND. | ND. | ND. |
| L-asparagine | 0 | ND. | ND. | ND. |
| L-aspartic acid | 0 | ND. | ND. | ND. |
| L-glutamic acid | 0 | ND. | ND. | ND. |
| L-glutamine | 0 | ND. | ND. | ND. |
| Glycine | 0 | ND. | ND. | ND. |
| L-histidine | 0 | ND. | ND. | ND. |
| L-isoleucine | 0 | ND. | ND. | ND. |
| L-lysine | 0 | ND. | ND. | ND. |
| L-methionine | 0 | ND. | ND. | ND. |
| L-ornithine | 0 | ND. | ND. | ND. |

Abbreviations:
ND.: not determined;
PfTDH: TDH from *Pyrococcus furiosus*;
AgTDH: TDH from *Arthrobacter globiformis*;
GdTDH: TDH from chicken liver (*Gallus domesticus*)

| | Relative activity (%) | | | | |
|---|---|---|---|---|---|
| Substrate | CnTDH | CyTDH | CsTDH | EcTDH | StTDH |
| Amino acids | | | | | |
| L-phenylalanine | 0 | 0 | 0 | ND. | ND. |
| L-proline | 0 | 0 | 0 | ND. | ND. |
| Taurine | 0 | ND. | ND. | ND. | ND. |
| L-tryptophan | 0 | 0 | 0 | ND. | ND. |
| L-tyrosine | 0 | 0 | 0 | ND. | ND. |
| L-valine | 0 | 0 | 0 | ND. | ND. |
| Alcohols | | | | | |
| Glycerol | 0 | ND. | ND. | ND. | ND. |
| 1-Butanol | 0 | ND. | ND. | ND. | ND. |
| 2-Butanol | 0 | 0 | ND. | ND. | ND. |
| 1,2-Butanediol | 0 | ND. | ND. | ND. | ND. |
| 1,3-Butanediol | 0 | ND. | ND. | ND. | ND. |
| 2,3-Butanediol | 0 | ND. | ND. | ND. | ND. |

TABLE 5-continued

| Amino alcohols | | | | | |
|---|---|---|---|---|---|
| DL-2-amino1-butanol | 0 | ND. | ND. | ND. | ND. |
| Other | | | | | |
| L-threonine methyl ester | 0 | ND. | 0 | 27 | ND. |
| L-threonine amide | 0 | ND. | 0 | 98 | ND. |
| L-threonine hydroxide | 0 | ND. | 0 | 25 | ND. |
| DL-α-amino-β-hydroxyvaleric acid | ND. | 31 | 20 | 71 | ND. |
| DL-threo-3-phenylserine | 0 | 0 | 0 | 3 | ND. |
| Acetoin | 0 | ND. | 0 | ND. | ND. |

Abbreviations:
ND.: not determined;
CyTDH: TDH from *Cytophaga* sp. KUC-1;
CsTDH: TDH from *Clostridium sticklandii*;
EcTDH: TDH from *Escherichia coli* K-12;
StTDH: TDH from *Streptomyces* sp. 139;

| | Relative activity (%) | | | |
|---|---|---|---|---|
| Substrate | PfTDH | AgTDH | TkTDH | GdTDH |
| Amino acids | | | | |
| L-phenylalanine | 0 | ND. | ND. | ND. |
| L-proline | 0 | ND. | ND. | ND. |
| Taurine | ND. | ND. | ND. | ND. |
| L-tryptophan | 0 | ND. | ND. | ND. |
| L-tyrosine | 0 | ND. | ND. | ND. |
| L-valine | 0 | ND. | ND. | ND. |
| Alcohols | | | | |
| Glycerol | 4 | ND. | ND. | ND. |
| 1-Butanol | 0 | ND. | ND. | ND. |
| 2-Butanol | 0 | ND. | ND. | ND. |
| 1,2-Butanediol | 52 | ND. | ND. | ND. |
| 1,3-Butanediol | 0 | ND. | ND. | ND. |
| 2,3-Butanediol | 94 | ND. | ND. | ND. |
| Amino alcohols | | | | |
| DL-2-amino1-butanol | ND. | ND. | ND. | ND. |
| Other | | | | |
| L-threonine methyl ester | ND. | ND. | ND. | ND. |
| L-threonine amide | ND. | ND. | ND. | ND. |
| L-threonine hydroxide | ND. | ND. | ND. | ND. |
| DL-α-amino-β-hydroxyvaleric acid | ND. | ND. | ND. | 0 |
| DL-threo-3-phenylserine | ND. | ND. | ND. | ND. |
| Acetoin | 38 | ND. | ND. | ND. |

Abbreviations:
ND.: not determined;
PfTDH: TDH from *Pyrococcus furiosus*;
AgTDH: TDH from *Arthrobacter globiformis*;
GdTDH: TDH from chicken liver (*Gallus domesticus*)

Kinetic Constants of TDH

Figure 7:
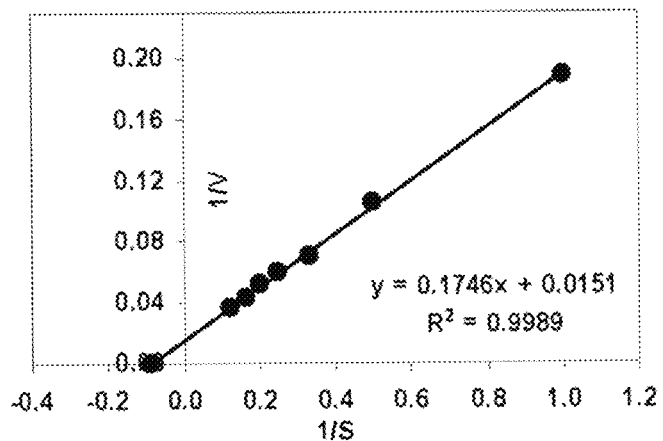
FIG. 7 is a Lineweaver Burk plot of the TDH of the present invention for L-threonine.
Figure 8:
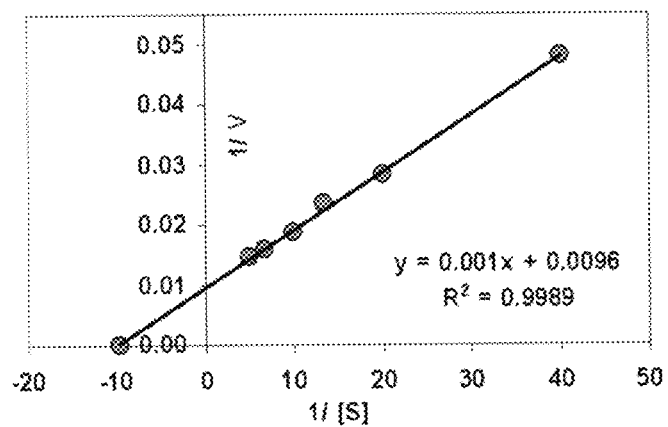
FIG. 8 is a Lineweaver Burk plot of the TDH of the present invention for $NAD^+$.

The kinetic constants relative to L-threonine and NAD+ were determined by using a Lineweaver Burk plot. At an NAD+ concentration of 2.5 mM, the maximum rate (Vmax) and Michaelis constant (Km) relative to L-threonine were 11.6 mM and 66.3 μmol/mg/minute, respectively (FIG. 7). The Vmax and Km relative to NAD+ at an L-threonine concentration of 10 mM were 0.1 mM and 104.2 μmol/mg/minute, respectively (FIG. 8).

The Effect of Various Compounds on Enzymatic Activity

Purified TDH was maintained at 30° C. for 1 hour with various metal ions (final concentration 1 mM) or inhibitors (final concentration 10 mM). The residual activity was measured and represented as the relative value to the activity of the enzyme without the additives. The activity was measured at optimal pH and temperature.

Results

The effects of metal ions (Table 6). The enzyme was partially inhibited by $FeCl_3$, $FeCl_2$, and $SnCl_2$ and the residual activity levels following 1 hour at constant temperature were 27, 68, and 84%, respectively.

TABLE 6

The effect of metal ions on TDH activity

| Metal compound | Relative activity | Metal compound | Relative activity |
|---|---|---|---|
| $FeCl_3$ | 27 | $CuSO_4$ | 115 |
| $FeCl_2$ | 68 | $CoCl_2$ | 115 |
| $SnCl_2$ | 84 | $NiCl_2$ | 119 |
| $MnCl_2$ | 102 | $AgNO_3$ | 100 |
| $MnSO_4$ | 114 | LiCl | 109 |
| $ZnCl_2$ | 105 | $CrCl_3$ | 110 |
| $ZnSO_4$ | 109 | $PbCl_2$ | 118 |
| $CaCl_2$ | 109 | CsCl | 117 |
| $MgCl_2$ | 112 | $BaCl_2$ | 113 |
| $MgSO_4$ | 112 | $AlCl_3$ | 118 |
| $CuCl_2$ | 117 | $NaMoO_4$ | 113 |

As shown in Table 7, TDH activity was not inhibited by metal chelating agents such as EDTA and EGTA. Metal ions were not thought to be necessary as cofactors. Even when dialyzed against a buffer containing 10 mM of EDTA, enzymatic activity survived. Nor did the reducing agents β-mercaptoethanol and DTT inhibit enzymatic activity. For $K[Fe(CN)_6]$, $K_3[Fe(CN)_6]$, and calcium pantothenate, there was slight inhibiting. The residual activity levels following iodoacetic acid, PMSF/isopropanol, PCMB, $HgCl_2$, and $NaN_3$ processing were 48%, 37%, 6.2%, 23%, and 12%, respectively. Enzymatic activity was inhibited by iodoacetamide, PMS, and NEM.

TABLE 7

The effect of inhibitors on TDH activity

| Inhibitor | Relative activity (%) | Inhibitor | Relative activity (%) |
|---|---|---|---|
| None | 100 | | |
| EDTA | 103 | Calcium pantothenate | 95.0 |
| EGTA | 94 | Iodoacetic acid | 48.0 |
| DEPC | 92 | Iodoacetamide | 0.8 |
| DTT | 125 | PMSF/isopropanol | 37.0 |
| β-mercaptoethanol | 114 | PCMB | 6.2 |
| Trypsin chymotrypsin inhibitor T-9777 | 105 | PMS | 0.0 |
| Trypsin inhibiter T-9378 | 101 | $HgCl_2$ | 23.0 |
| $K_3[Fe(CN)_6]$ | 75 | $NaN_3$ | 12.0 |
| $K[Fe(CN)_6]$ | 96 | NEM | 0.0 |

Cloning the L-threonine hydrogenase gene derived from *Cupriavidus necator* NBRC 102504 (SEQ ID No.2)

Gene cloning and expression were successfully conducted based on information from the N-terminal amino acid sequence (15 residues) of purified TDH.

Cloning of TDH gene from *Cupriavidus necator*

*C. necator* was cultured for 24 hours at 300 rpm and 30° C. using 5 mL of TGY medium. Genomic DNA of *C. necator* was prepared from the cells. The amino acid sequence of the N-terminus of the purified TDH enzyme was analyzed and a search for similar sequences was conducted in the database. Based on the results, the following set of primers was designed:

TDH-N1: 5'-<u>ATG</u>GARGCNGGNAARCCNAAR-3' (SEQ ID NO: 3)

TDH-C1: 5'-RAADATRTCNACNGCRTARTC-3' (SEQ ID NO: 4)

The TDH-N1 primer contained the start codon ATG, which is underlined. The PCR solution contained 200 pmol of TDH-N1, 100 pmol of TDH-C1, 23.5 ng of genomic DNA, 0.25 µL of TaKaRa Ex Taq (5 units/µL), 5 µL of 10×Ex Taq buffer, 4 µL of dNTP mixture (2.5 mM, respectively) in 50 µL. In PCR, 30 cycles of denaturation for 10 seconds at 98° C. (60 seconds in initial cycle only), annealing for 30 seconds at 55° C., and elongation for 180 seconds at 72° C. were conducted. The amplified PCR product of about 550 bp was extracted from agarose gel. It was extracted using a Gel-M™ gel extraction kit made by Viogene (Sunnyvale, Calif.). T4 ligase (New England Biolabs Japan, Tokyo) was used for ligation to a pT7-Blue T vector. The gene sequence was analyzed with an ABI Prism 310 Gene Analyzer (Applied Biosystems Japan, Tokyo). Inverse PCR was used to analyze the gene sequence upstream and downstream from this 550 bp region. A group of primers such as the following was designed based on the gene sequence that was decoded:

TDH-N1: 5'-GTTGAGCATCTCGTGCGTCA-3' (SEQ ID NO: 5)

TDH-C1: 5'-ACGGTCTACGGCATCTCCAA-3' (SEQ ID NO: 6)

Genomic DNA (15 µg) of *C. necator* was digested with EcoRI, extracted with phenol chloroform, and precipitated from ethanol. The product was dissolved in 30 µL of TE buffer and left to undergo a self-ligation reaction for 12 hours at 16° C. The circular DNA (2 µL) was subjected to PCR employing TDH-N1 and TDH-C1 as primer and GC buffer under the following conditions. That is, 30 cycles of denaturation for 30 seconds at 94° C. (60 seconds in initial cycle only), annealing for 60 seconds at 60° C., and elongation for 120 seconds at 72° C. were conducted. The roughly 500 bp amplified fragment obtained was digested with EcoRI. Following cloning, the gene sequence was analyzed. The gene contained a gene sequence comprising an N-terminus and a stop codon. The primer walking technique was employed to amplify the entire gene using the following set of primers:

CnTDH-F: 5'-GAATT<u>CATATG</u>GAAGCTGGCAAACCGAAG-3' (SEQ ID NO: 7)

CnTDH-R: 5'-AGTAT<u>GGATCC</u>TCAGCCCGCCAGCGTGGCCT-3' (SEQ ID NO: 8)

CnTDH-F has a start codon at the NdeI recognition site (double underlined). CnTDH-R has a stop codon at the BamHI recognition side (double underlined). PCR was conducted as set forth above with TaKaRa Ex Taq. The TDH gene (957 bp) was subcloned into pET15b, yielding the plasmid CnTDHpET15b. This plasmid was then used to transform *E. coli* JM109. The *E. coli* transformant was cultured for 12 hours at 37° C. in LB medium. The plasmid CnTDHpET15b was extracted from the *E. coli* transformant, and *E. coli* BL21 (DE3) was transformed to express the enzyme.

Results

The DNA sequence (SEQ ID NO: 2) of TDH was examined. The TDH gene coded for 318 amino acids (FIG. 9). The molecular weight was calculated to be 34,627.85. The molecular weight of the subunit was calculated to be 37,200 by SDS-PAGE analysis.

Expression and Purification of TDH Enzyme Protein

*E. coli* transformant containing pET15bBL21 was cultured and the TDH that was expressed was purified. In LB medium containing 5 mL of 0.2 mM ampicillin, aerobic preculturing was conducted for 12 hours at 37° C. A 500 mL quantity of the medium was transplanted and cultured aerobically for 12 hours at 37° C. IPTG was then added to 0.5 mM and culturing was conducted for another 4 hours. The *E. coli* was centrifuged for 10 minutes at 4° C. and 5,000×g and washed twice with physiological saline. The *E. coli* was ultrasonically treated by using the conventional method. The cell-free extract obtained was passed through a Ni-Sepharose™-6 Fast Flow column (GE Healthcare, Buckinghamshire, UK), washed with 20 mM potassium phosphate buffer (pH 8.0) containing 0.3M NaCl and 75 mM imidazole, and eluted with the same buffer containing 500 mM of imidazole. The active fraction was dialyzed against a 20 mM potassium phosphate buffer (pH 8.0).

Results

Figure 10:
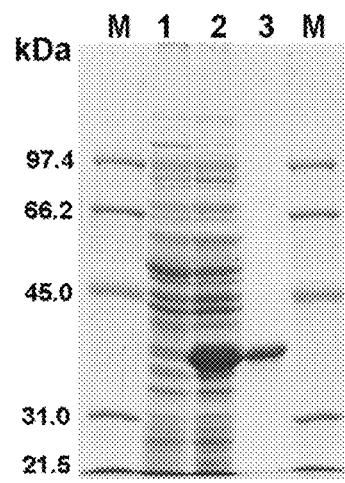
FIG. 10 shows an SDS-PAGE of TDH-His purified from *Escherichia coli* (*E. coli*) containing plasmid CnTDHpET15b. Lane M: low molecular weight marker; Lane 1: cell-free extract of *E. coli* BL21 (DE3); Lane 2: cell-free extract of CnTDH-His from *E. coli* BL21 (DE3); Lane 3: purified genetically recombinant TDH-His enzyme.

The recombinant TDH-His that was expressed in *E. coli* BL21 (DE3) contained plasmid CnTDHpET15b had an His-tag on the N-terminus, and was produced under the described optimal culture conditions. In 500 mL of culture, 6,000 U of TDH were expressed. The cell-free extract exhibited a specific activity of 15.3 U/mg. Single-step purification was conducted by Ni-chelating column chromatography, and a single band was observed in SDS-PAGE (FIG. 10). The specific activity of the purified recombinant enzyme was 64.5 U/mg (Table 8). This specific activity was about 1.5-fold that of the purified enzyme from the wild strain (42.2 U/mg). The purification yield was 98%.

TABLE 8

Table 8. Purification steps of recombinant CnTDH-His

| Step | Total volume (mL) | Total activity (U) | Total protein (mg) | Specific activity (U/mg) | Yield (%) | Purification (fold) |
|---|---|---|---|---|---|---|
| Cell-free extraction | 17 | 6,028 | 394 | 15.3 | 100 | 1.0 |
| Ni-Sepharose | 78 | 5,886 | 91 | 65 | 98 | 4.2 |

Quantification of L-threonine with TDH

Sample preparation

Commercially available human (serum and plasma) samples were employed. The protein and the like were removed by ultrafiltration (Centriprep YM-10) at 4° C. and the filtrate was stored at −20° C. until use.

Standard L-threonine

L-threonine solutions (0 to 3,000 µM) were stored in a freezer at −20° C.

Quantifying L-threonine using a microplate reader

Quantification was conducted with a 96-well UV microplate spectrophotometer. It contained a total reaction volume of 200 µL and consisted of 100 mM glycine KCl—KOH buffer (pH 10.0), 2.5 mM NAD$^+$, and deproteinized sample. The reaction began with the addition of the enzyme. The mixture was maintained at a constant temperature of 30° C. for 10 to 30 minutes and absorbance at 340 nm at the endpoint was measured by microplate spectrophotometer. The change in absorbance (ΔA) was calculated by subtracting a control value from the final absorbance and three consecutive tests were conducted.

Results

Figure 11:
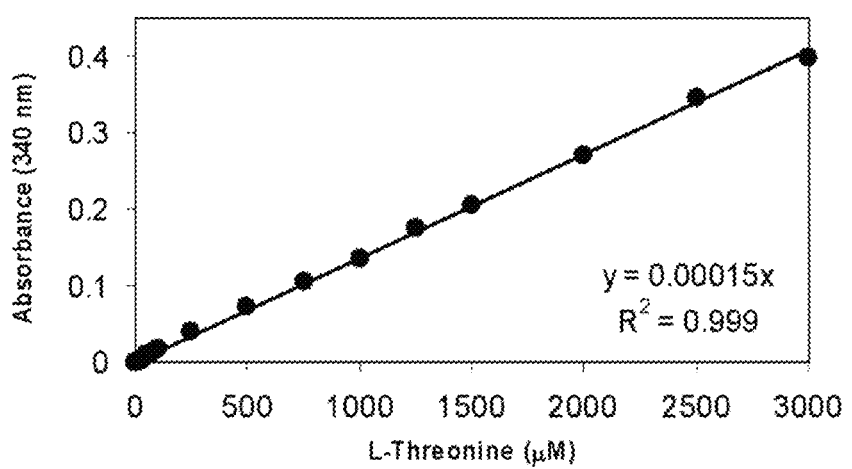
FIG. 11 shows an enzymatic quantitative calibration curve of L-threonine using TDH.

The enzyme quantification calibration curve of L-threonine employing TDH exhibited a linear concentration for 10 to 3,000 μM (FIG. 11).

Figure 12:
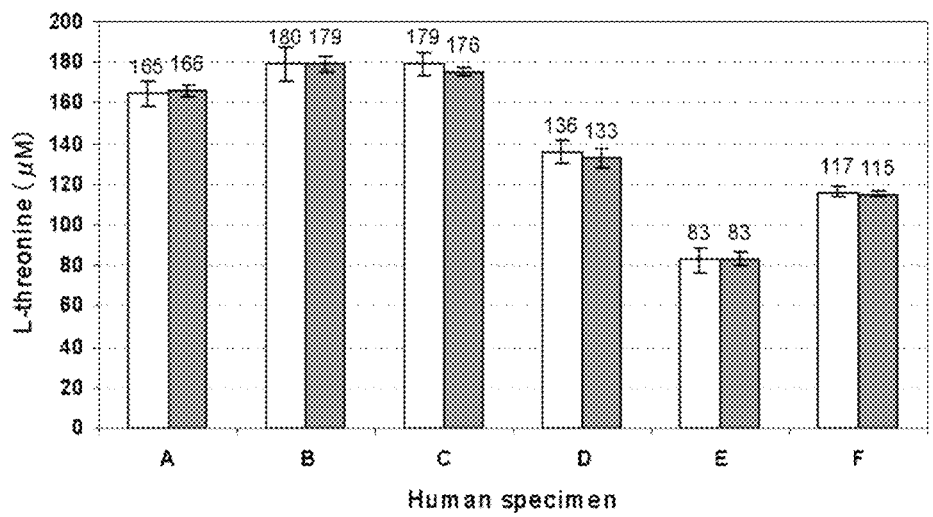
FIG. 12 shows the results of measurement of the concentration of L-threonine in human blood. Enzymatic microplate assay employing TDH (□), quantification by UPLC (■), Samples: A: human serum-A; B: human serum-B; C: pooled human serum; D: human plasma-D; E: human plasma-E; F: pooled human plasma.

The concentration of L-threonine in each six human-derived sample was quantified using an enzymatic method with UV microplate spectrophotometer, and the result of the quantification was compared to that by using ultra performance liquid chromatography (UPLC) (FIG. 12). The enzyme assay and UPLC assay yielded roughly the same values, indicating that the enzymatic assay system used in this study was reliable.

Figure 13:
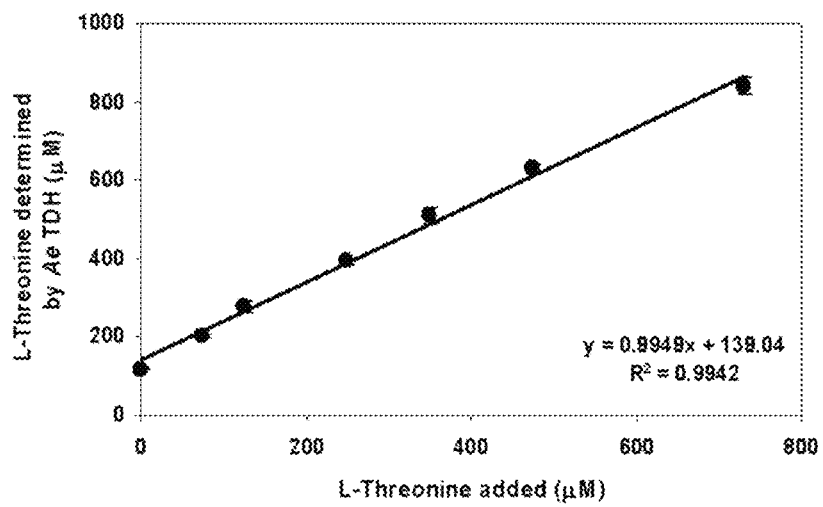
FIG. 13 shows the results of quantification of L-threonine enzyme in the course of adding a known quantity of L-threonine to human plasma.

The reliability of the enzymatic quantification method was examined by measuring L-threonine at various concentrations in human plasma. As shown in FIG. 13, a good correlation of ($R^2$=0.9942) was achieved. The L-threonine recovery rate under these assay conditions was 99.5%.

As shown in Table 9, the precision of the L-threonine quantification in human samples (n=12) was represented as a C.V. within the assays of 2.2 to 6.2%. A C.V. between assays thereof was 1.4 to 2.9%.

TABLE 9

Table 9. Precision of L-threonine quantification with TDH

| | Within-run (n = 12) | | Between-run (n = 5) | |
|---|---|---|---|---|
| Sample | Mean ± S.D. | C.V. (%) | Mean ± S.D. | C.V. (%) |
| A | 163.1 ± 4.7 | 2.9 | 166.1 ± 4.2 | 2.5 |
| B | 176.9 ± 5.1 | 2.9 | 175.8 ± 3.0 | 1.7 |
| C | 175.5 ± 3.9 | 2.2 | 175.4 ± 2.5 | 1.4 |
| D | 134.6 ± 4.5 | 3.3 | 134.6 ± 2.0 | 1.5 |
| E | 86.3 ± 5.4 | 6.2 | 86.1 ± 2.5 | 2.9 |
| F | 115.3 ± 3.6 | 3.1 | 115.1 ± 3.2 | 2.8 |

Assays of threonine deaminase (TD) derived from *Escherichia coli* and aldehyde dehydrogenase (ALDH) derived from yeast that have been reported in L-threonine enzyme quantification were compared to the TDH method (Table 10).

TABLE 10

A comparison of L-threonine quantification methods

| | CnTDH assay (present invention) | ALDH assay | TD assay |
|---|---|---|---|
| Sample preparation | Plasma, serum samples Ultrafiltration by deproteinizing Centricon YM-10 | Plasma Deproteinization with perchloric acid (3.5%) Neutrization (5N KOH) | Culture media Activated charcoal processing pH is rendered neutral |
| Substrate specificity | L-threonine | L-threonine | L-threonine L-serine D-serine |
| Preprocessing | None | Sample dilution (threonine quantity 10 to 50 μM) Periodate oxidation | None |
| Quantification range (μM) | 10-3000 | 10-500 | — |
| Recovery rate (%) | 99.4 | 95.0 | — |
| Precision (%) | 1.4-6.2 | 4.9 | 3.6 |

The new microplate assay of the present invention employing TDH was found to be an extremely reliable quantification method as compared even to UPLC quantification. Further, the TDH microplate method exhibited high precision and a broad quantification range as compared to known methods. The method of the present invention is suited to the measurement of the L-threonine concentration in the body, such as in human blood, and in foods.

REFERENCE DOCUMENTS

[1] Newman E B, Kapoor V, Potter R. Role of L-threonine dehydrogenase in the catabolism of threonine and synthesis of glycine by *Escherichia coli*. J. Bacteriol. (1976) 126:1245-1249.

[2] Yuan J H, Austic R E. Characterization of hepatic L-threonine dehydrogenase of chicken. Comp. Biochem. Physiol. (2001) 130:65-73.

[3] Marcus J P, Dekker E E. Threonine formation via the coupled activity of 2-amino-3-ketobutyrate coenzyme A lyase and threonine dehydrogenase. J. Bacteriol. (1993) 175:6505-6511.

[4] McGilvray D, Morris J G. L-Threonine dehydrogenase (Arthorbacter). Method in Enzymology. (1971) 17:580-584.

[5] Kazuoka T, Takigawa S, Arakawa N, Hizukuri Y, Muraoka I, Oikawa T, Soda K. Novel Psychrophilic and thermolabile L-threonine dehydrogenase from *Psychrophilic Cytophaga* sp. strain KUC-1. J. Bacteriol. (2003) 15:4483-4489.

[6] Wagner M, Andreesen J R. Purification and characterization of threonine dehydrogenase from *Clostridium sticklandii*. Arch. Microbiol. (1995) 163:286-290.

[7] Machielsen R, van der Oost J. Production and characterization of a thermostable L-threonine dehydrogenase from the hyperthermophilic archaeon *Pyrococcus furiosus*. FEBS J. (2006) 273:2722-2729.

[8] Higashi N, Tanimoto K, Nishioka M, Ishikawa K, Taya M. Investigating a catalytic mechanism of hyperthermophilic L-threonine dehydrogenase from *Pyrococcus horikoshii*. J. Biochem. (2008) 144:77-85.

[9] Bashir Q, Rashid N, Jamil F, Imanaka T, Akhtar M. Highly thermostable L-threonine dehydrogenase from the hyperthermophilic archaeon *Thermococcus kodakaraensis*. J. Biochem. (2009) 146:95-102.

[10] Bao Y, Xie H, Shan J, Jiang R, Zhang Y, Guo L, Zhang R, Li Y. Biochemical characteristics and function of a threonine dehydrogenase encoded by step 11 in Ebosin biosynthesis of *Streptomyces* sp. 139. J. Appl. Microbiol. (2009) 106:1140-1146.

[11] Aronson B D, Somerville R L, Epperly B R, Dekker E E. The primary structure of *Escherichia coli* L-threonine dehydrogenase. J. Biol. Chem. (1989) 264:5226-5232.

[12] Ishikawa K, Higashi N, Nakamura T, Matsuura T, Nakagawa A. The first crystal structure of L-threonine dehydrogenase. J. Mol. Biol. (2007) 366:857-867.

The entire contents of Reference Documents 1 to 12 are incorporated herein particularly by reference.

INDUSTRIAL APPLICABILITY

The present invention is useful in fields requiring the measurement of L-threonine concentration in the biological material, such as in human blood, and in food.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for analyzing the L-threonine contained in a specimen, comprising:
   A) mixing a sample comprising a specimen and L-threonine dehydrogenase, with the coenzyme NAD$^+$; and
   B) determining the quantity of a product after a time period,
   wherein the product is selected from the group consisting of NADH and 2-amino-3-oxybutyric acid;
   wherein said L-threonine dehydrogenase has L-threonine dehydrogenase activity that is oxidative and specific for L-threonine to 2-amino-3-oxobutyric acid, and is selected from the group consisting of:
   (i) L-threonine dehydrogenase from *Cupriavidus necator*;
   (ii) a protein comprising the amino acid sequence of SEQ ID NO: 1;
   (iii) a protein comprising the amino acid sequence of SEQ ID NO: 1, but having from 1 to 30 amino acid deletions, substitutions, and/or additions; and
   (iv) a protein comprising an amino acid sequence having 90% or greater homology with the amino acid sequence of SEQ ID NO: 1.

2. The method according to claim 1, wherein the L-threonine dehydrogenase is from *Cupriavidus necator*.

3. The method of claim 2, wherein the L-threonine dehydrogenase is from *Cupriavidus necator* NBRC 102504 (SEQ ID NO: 1).

4. The method according to claim 1, wherein said determining is by a method selected from the group consisting of:
   A) measuring absorbance in the sample to obtain the quantity of NADH,
   B) observing the pigment generated by oxidation of NADH or by using electron carriers in a NADH$^-$ tetrazolium system, and
   C) measuring fluorescence of a fluorescent pigment generated by NADH to obtain the quantity of NADH.

5. The method of claim 1, wherein said determining comprises allowing the sample to produce amino acetone from the 2-amino-3-oxobutyric acid, mixing the resulting product with monoamine oxidase to produce ammonia and hydrogen peroxide, and measuring the quantity of the ammonia or hydrogen peroxide.

* * * * *

SEQUENCE LISTING

<160> NUMBER OF SEQ ID NOS: 8

<210> SEQ ID NO 1
<211> LENGTH: 318
<212> TYPE: PRT
<213> ORGANISM: Cupriavidus necator

<400> SEQUENCE: 1

| | | | | | | | | | | | | | | | |
|---|---|---|---|---|---|---|---|---|---|---|---|---|---|---|---|
| Met | Glu | Ala | Gly | Lys | Pro | Lys | Ile | Leu | Ile | Val | Gly | Ala | Asn | Gly | Gln |
| 1 | | | | 5 | | | | | 10 | | | | | 15 | |
| Ile | Gly | Ser | Glu | Leu | Ala | Leu | Ala | Leu | Ala | Glu | Arg | Tyr | Gly | Arg | Thr |
| | | | 20 | | | | | 25 | | | | | 30 | | |
| Asn | Val | Ile | Thr | Ser | Asp | Val | Val | Pro | Thr | Gly | Arg | His | Val | His | Leu |
| | | | | 35 | | | | | 40 | | | | | 45 | |
| Thr | His | Glu | Met | Leu | Asn | Ala | Thr | Asp | Arg | Gly | Glu | Leu | Ala | Thr | Val |
| | 50 | | | | | 55 | | | | | 60 | | | | |
| Val | Glu | Arg | His | Gly | Ile | Thr | Gln | Val | Tyr | Leu | Leu | Ala | Ala | Ala | Leu |
| 65 | | | | | 70 | | | | | 75 | | | | | 80 |
| Ser | Ala | Thr | Gly | Glu | Lys | Ala | Pro | Gln | Trp | Ala | Trp | Asn | Leu | Asn | Met |
| | | | | 85 | | | | | 90 | | | | | 95 | |
| Thr | Ser | Leu | Leu | Asn | Val | Leu | Glu | Leu | Ala | Arg | Gln | Thr | Gly | Leu | Glu |
| | | | 100 | | | | | 105 | | | | | 110 | | |
| Arg | Val | Phe | Trp | Pro | Ser | Ser | Ile | Ala | Ala | Phe | Gly | Pro | Thr | Thr | Pro |
| | | | | 115 | | | | | 120 | | | | | 125 | |
| Ala | Gly | Gln | Thr | Pro | Gln | Lys | Thr | Val | Met | Glu | Pro | Thr | Thr | Val | Tyr |
| | 130 | | | | | 135 | | | | | 140 | | | | |
| Gly | Ile | Ser | Lys | Gln | Ala | Gly | Glu | Gly | Trp | Cys | Arg | Trp | Tyr | His | Ala |
| 145 | | | | | 150 | | | | | 155 | | | | | 160 |
| Asn | His | Gly | Val | Asp | Val | Arg | Ser | Val | Arg | Tyr | Pro | Gly | Leu | Ile | Ser |
| | | | | 165 | | | | | 170 | | | | | 175 | |
| His | Lys | Thr | Pro | Pro | Gly | Gly | Gly | Thr | Thr | Asp | Tyr | Ala | Val | Asp | Ile |
| | | | 180 | | | | | 185 | | | | | 190 | | |
| Phe | His | Ala | Ala | Val | Thr | Gly | Glu | Pro | Tyr | Thr | Cys | Phe | Leu | Lys | Glu |
| | | | | 195 | | | | | 200 | | | | | 205 | |
| Asp | Glu | Ala | Leu | Pro | Met | Met | Tyr | Met | Pro | Asp | Ala | Ile | Arg | Ala | Thr |
| | 210 | | | | | 215 | | | | | 220 | | | | |
| Ile | Glu | Leu | Met | Glu | Ala | Pro | Ala | Asp | Lys | Leu | Ser | Glu | Arg | Gly | Ser |
| 225 | | | | | 230 | | | | | 235 | | | | | 240 |
| Tyr | Asn | Ile | Ala | Gly | Met | Ser | Phe | Thr | Pro | Ala | Gln | Ile | Ala | Ala | Ala |
| | | | | 245 | | | | | 250 | | | | | 255 | |
| Ile | Arg | Glu | Gln | Val | Pro | Gly | Phe | Gln | Ile | Arg | Tyr | Glu | Pro | Asp | Tyr |
| | | | 260 | | | | | 265 | | | | | 270 | | |
| Arg | Gln | Ala | Ile | Ala | Gln | Gly | Trp | Pro | Asp | Ser | Ile | Asp | Asp | Ser | Val |
| | | | | 275 | | | | | 280 | | | | | 285 | |
| Ala | Arg | Ala | Asp | Trp | Gly | Trp | Lys | Ala | Gln | Tyr | Gly | Leu | Lys | Glu | Met |
| | 290 | | | | | 295 | | | | | 300 | | | | |
| Val | Ala | Asp | Met | Leu | Ala | Asn | Leu | Lys | Ala | Thr | Leu | Ala | Gly | | |
| 305 | | | | | 310 | | | | | 315 | | | | | |

<210> SEQ ID NO 2
<211> LENGTH: 957
<212> TYPE: DNA
<213> ORGANISM: Cupriavidus necator

<400> SEQUENCE: 2
atggaagctg gcaaaccgaa gatcctgatt gtcggcgcca acggccagat cgggtctgaa    60

| | |
|---|---|
| ctggcactgg cgctggccga gcgctacggg cgcaccaacg tgatcacctc cgacgtggtg | 120 |
| cccaccggcc gccatgtgca tctgacgcac gagatgctca acgccaccga ccgcggcgag | 180 |
| ctggccaccg tggtcgagcg ccatggcatc acccaggtct acctgctggc cgccgcgctg | 240 |
| tccgccaccg gcgaaaaggc gccacagtgg gcctggaacc tcaatatgac cagcctgctc | 300 |
| aatgtgctgg agctggcgcg gcagaccggg ctggagcggg tgttctggcc aagctcgatt | 360 |
| gcagccttcg gcccgaccac gcctgccgga cagacaccgc agaagaccgt gatggagccc | 420 |
| accacggtct acggcatctc caagcaggcg ggcgagggtt ggtgccgctg gtatcacgcc | 480 |
| aaccacggcg tggatgtgcg cagcgtgcgc tatccgggcc tgatctcgca caagacgcca | 540 |
| cccggcggcg gcaccaccga ctatgcggtc gacatcttcc atgcggcggt gacgggcgag | 600 |
| ccctacacct gcttcctgaa ggaagacgaa gccctgccga tgatgtatat gcccgatgcg | 660 |
| atccgcgcca ccatcgaact gatggaagcc ccggcggaca agctgagcga gcgcggcagc | 720 |
| tacaacatcg ccggcatgag cttcacgccc gcgcagatcg ccgcggccat ccgcgagcag | 780 |
| gtgccgggct tccagatccg ctatgaaccc gactatcgcc aggcgattgc gcagggctgg | 840 |
| ccggattcga tcgatgattc ggtcgcgcgc gcggactggg ggtggaaggc ccagtatgga | 900 |
| ctgaaggaga tggtcgcgga catgcttgcc aacctgaagg ccacgctggc gggctga | 957 |

<210> SEQ ID NO 3
<211> LENGTH: 21
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
atggargcng gnaarccnaa r                                          21

<210> SEQ ID NO 4
<211> LENGTH: 21
<212> TYPE: DNA
<213> ORGANISM: Artificial sequence
<220> FEATURE:
<223> OTHER INFORMATION: Synthesized
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 4
raadatrtcn acngcrtart c                                          21

<210> SEQ ID NO 5
<211> LENGTH: 20
<212> TYPE: DNA

```
<213> ORGANISM: Artificial sequence
<220> FEATURE:
<223> OTHER INFORMATION: Synthesized

<400> SEQUENCE: 5
gttgagcatc tcgtgcgtca                                              20

<210> SEQ ID NO 6
<211> LENGTH: 20
<212> TYPE: DNA
<213> ORGANISM: Artificial sequence
<220> FEATURE:
<223> OTHER INFORMATION: Synthesized

<400> SEQUENCE: 6
acggtctacg gcatctccaa                                              20

<210> SEQ ID NO 7
<211> LENGTH: 29
<212> TYPE: DNA
<213> ORGANISM: Artificial sequence
<220> FEATURE:
<223> OTHER INFORMATION: Synthesized

<400> SEQUENCE: 7
gaattcatat ggaagctggc aaaccgaag                                    29

<210> SEQ ID NO 8
<211> LENGTH: 31
<212> TYPE: DNA
<213> ORGANISM: Artificial sequence
<220> FEATURE:
<223> OTHER INFORMATION: Synthesized

<400> SEQUENCE: 8
agtatggatc ctcagcccgc cagcgtggcc t                                 31
```